(12) United States Patent
Levinson et al.

(10) Patent No.: US 11,166,671 B2
(45) Date of Patent: Nov. 9, 2021

(54) DIFFERENTIATION OF FLUID VOLUME CHANGE

(71) Applicant: Cerebrotech Medical Systems, Inc., Pleasanton, CA (US)

(72) Inventors: Mitchell Elliott Levinson, Pleasanton, CA (US); Eugene Mark Shusterman, Pleasanton, CA (US); William L. Shea, Martinez, CA (US)

(73) Assignee: Cerebrotech Medical Systems, Inc., Pleasanton, CA (US)

( * ) Notice: Subject to any disclaimer, the term of this patent is extended or adjusted under 35 U.S.C. 154(b) by 1102 days.

(21) Appl. No.: 15/410,838

(22) Filed: Jan. 20, 2017

(65) Prior Publication Data

US 2017/0127946 A1 May 11, 2017

Related U.S. Application Data

(63) Continuation-in-part of application No. 14/844,681, filed on Sep. 3, 2015, now Pat. No. 10,743,815, which
(Continued)

(51) Int. Cl.
*A61B 5/00* (2006.01)
*A61B 5/05* (2021.01)
(Continued)

(52) U.S. Cl.
CPC .......... *A61B 5/4875* (2013.01); *A61B 5/0013* (2013.01); *A61B 5/0022* (2013.01);
(Continued)

(58) Field of Classification Search
None
See application file for complete search history.

(56) References Cited

U.S. PATENT DOCUMENTS 3,720,763 A 3/1973 Ishii
3,789,834 A 2/1974 Duroux
(Continued)

FOREIGN PATENT DOCUMENTS

AU 2015227382 B2 4/2017
CN 1158077 A 8/1997
(Continued)

OTHER PUBLICATIONS

Sun et al. "The detection of chronic cerebral hemorrhage in rabbits with magnetic induction." Journal of Physics: Conference Series. vol. 407. No 1. IOP Publishing, 2012. (10 pages).
(Continued)

*Primary Examiner* — Patricia J Park
(74) *Attorney, Agent, or Firm* — Merchant & Gould P.C.

(57) ABSTRACT

A method for detecting evidence of a stroke in a patient may involve securing a volumetric integral phase-shift spectroscopy (VIPS) device to the patient's head, transmitting a first signal from a first transmitter of the VIPS device through a left hemisphere of the patient's brain to a receiver of the VIPS device, transmitting a second signal from a second transmitter of the VIPS device through a right hemisphere of the patient's brain to the receiver, and detecting the evidence of the stroke, with the VIPS device.

8 Claims, 17 Drawing Sheets

Related U.S. Application Data is a continuation-in-part of application No. 14/690,985, filed on Apr. 20, 2015, now Pat. No. 10,335,054, which is a continuation of application No. 14/275,549, filed on May 12, 2014, now abandoned, which is a continuation of application No. 13/745,710, filed on Jan. 18, 2013, now Pat. No. 8,731,636.

(60) Provisional application No. 61/588,516, filed on Jan. 19, 2012, provisional application No. 62/281,781, filed on Jan. 22, 2016.

(51) Int. Cl.
| | |
|---|---|
| A61B 5/053 | (2021.01) |
| A61B 5/03 | (2006.01) |
| G16H 40/67 | (2018.01) |
| G16H 50/20 | (2018.01) |
| A61B 5/245 | (2021.01) |
| A61B 5/0522 | (2021.01) |
| A61B 6/03 | (2006.01) |

(52) U.S. Cl.
CPC ............ A61B 5/0042 (2013.01); A61B 5/031 (2013.01); A61B 5/05 (2013.01); A61B 5/0522 (2013.01); A61B 5/245 (2021.01); A61B 5/4064 (2013.01); A61B 5/4839 (2013.01); A61B 5/4848 (2013.01); A61B 5/4878 (2013.01); A61B 5/6803 (2013.01); A61B 5/6814 (2013.01); A61B 5/721 (2013.01); A61B 5/7214 (2013.01); A61B 5/7225 (2013.01); A61B 5/7257 (2013.01); A61B 5/7275 (2013.01); A61B 5/7282 (2013.01); A61B 6/032 (2013.01); G16H 40/67 (2018.01); G16H 50/20 (2018.01); A61B 2560/0223 (2013.01); A61B 2562/0223 (2013.01); A61B 2562/166 (2013.01); A61B 2562/182 (2013.01); A61B 2562/222 (2013.01); A61B 2576/026 (2013.01)

(56) References Cited

U.S. PATENT DOCUMENTS

| | | |
|---|---|---|
| 4,240,445 A | 12/1980 | Iskander et al. |
| 4,488,559 A | 12/1984 | Iskander |
| 4,690,149 A | 9/1987 | Ko |
| 4,819,648 A | 4/1989 | Ko |
| 5,001,436 A | 3/1991 | Scot et al. |
| 5,128,354 A | 7/1992 | Masuda et al. |
| 5,189,018 A | 2/1993 | Goldman et al. |
| 5,441,495 A | 8/1995 | Liboff et al. |
| 5,446,384 A | 8/1995 | Dumoulin |
| 5,617,861 A | 4/1997 | Ross et al. |
| 5,827,893 A | 10/1998 | Lurie et al. |
| 5,853,370 A | 12/1998 | Chance |
| 5,919,144 A | 7/1999 | Bridger |
| 6,102,905 A | 8/2000 | Baxter et al. |
| 6,126,595 A | 10/2000 | Amano et al. |
| 6,356,081 B1 | 3/2002 | Misic |
| 6,413,227 B1 | 7/2002 | Yost et al. |
| 6,723,047 B1 | 4/2004 | Yamamoto |
| 6,924,773 B1 | 8/2005 | Paratte |
| 7,122,012 B2 | 10/2006 | Bouton et al. |
| 7,251,521 B2 | 7/2007 | Seeber |
| 7,638,341 B2 | 12/2009 | Rubinsky et al. |
| 7,910,374 B2 | 3/2011 | Rubinsky et al. |
| 7,998,080 B2 | 8/2011 | Ben-Ari et al. |
| 8,101,421 B2 | 1/2012 | Rubinsky et al. |
| 8,109,899 B2 | 2/2012 | Sundstrom |
| 8,303,110 B1 | 11/2012 | Weaver et al. |
| 8,361,391 B2 | 1/2013 | Rubinsky et al. |
| 8,506,514 B2 | 8/2013 | Pedersen |
| 8,731,636 B2 | 5/2014 | Wyeth et al. |
| 8,808,190 B2 | 8/2014 | Rosell Ferrer et al. |
| 9,307,918 B2 | 4/2016 | Kinrot et al. |
| 9,357,970 B2 | 6/2016 | Clark et al. |
| 9,456,757 B1* | 10/2016 | Zheng .................. A61B 5/7282 |
| 10,335,054 B2 | 7/2019 | Wyeth |
| 10,743,815 B2 | 8/2020 | Wyeth et al. |
| 2001/0034478 A1 | 10/2001 | Lambert et al. |
| 2003/0191409 A1 | 10/2003 | Yost et al. |
| 2003/0199784 A1 | 10/2003 | Lenhardt |
| 2005/0054939 A1 | 3/2005 | Ben-Ari et al. |
| 2005/0065422 A1 | 3/2005 | Kandori |
| 2005/0107685 A1 | 5/2005 | Seeber |
| 2005/0119716 A1 | 6/2005 | McClure |
| 2006/0116600 A1 | 6/2006 | Vesely et al. |
| 2007/0032827 A1 | 2/2007 | Katims |
| 2008/0177163 A1 | 7/2008 | Wang et al. |
| 2008/0183064 A1 | 7/2008 | Chandonnet et al. |
| 2008/0224688 A1 | 9/2008 | Rubinsky et al. |
| 2009/0105605 A1 | 4/2009 | Abreu |
| 2009/0234245 A1* | 9/2009 | Jaffe .................. A61B 5/0059 600/561 |
| 2010/0021035 A1* | 1/2010 | Gupta .................. G06T 7/0012 382/131 |
| 2010/0030293 A1 | 2/2010 | Sarkar et al. |
| 2010/0277163 A1 | 11/2010 | Nakamura et al. |
| 2011/0193575 A1 | 8/2011 | Rubinsky et al. |
| 2011/0267074 A1 | 11/2011 | Xie |
| 2012/0083717 A1 | 4/2012 | Alleman et al. |
| 2012/0101326 A1 | 4/2012 | Simon |
| 2012/0203134 A1 | 8/2012 | Kinrot |
| 2012/0245442 A1* | 9/2012 | Ukawa ............... A61B 5/14551 600/324 |
| 2013/0187666 A1 | 7/2013 | Rubinsky et al. |
| 2013/0190599 A1* | 7/2013 | Wyeth .................. G16H 50/20 600/409 |
| 2013/0274615 A1 | 10/2013 | Ben-Ari et al. |
| 2014/0243647 A1 | 8/2014 | Clark |
| 2014/0249400 A1 | 9/2014 | Wyeth |
| 2014/0371545 A1 | 12/2014 | Ben-Ari et al. |
| 2015/0209174 A1 | 7/2015 | Abreu |
| 2015/0223722 A1 | 8/2015 | Wyeth |
| 2015/0313496 A1 | 11/2015 | Connor |
| 2015/0374292 A1 | 12/2015 | Wyeth |
| 2016/0007879 A1* | 1/2016 | Gonzalez ............. A61B 5/0537 600/306 |
| 2016/0310054 A1* | 10/2016 | Izzetoglu ............. A61B 5/4878 |
| 2017/0055839 A1 | 3/2017 | Levinson |
| 2017/0319099 A1 | 11/2017 | Levinson |
| 2018/0064364 A1 | 3/2018 | Oziel |
| 2019/0021627 A1 | 1/2019 | Elliott |
| 2019/0365274 A1 | 12/2019 | Wyeth |
| 2021/0169413 A1 | 6/2021 | Wyeth |

FOREIGN PATENT DOCUMENTS

| | | |
|---|---|---|
| CN | 101052347 A | 10/2007 |
| CN | 102159129 A | 8/2011 |
| CN | 102481435 A | 5/2012 |
| CN | 203000923 U | 6/2013 |
| CN | 103442634 A | 12/2013 |
| CN | 103598883 A | 2/2014 |
| EP | 2111787 A1 | 10/2009 |
| GB | 2396421 | 6/2004 |
| JP | S56-27509 | 3/1981 |
| JP | S60-37905 | 3/1985 |
| JP | H01-212341 | 8/1989 |
| JP | 05-237073 | 9/1993 |
| JP | 2001-502832 | 2/2001 |
| JP | 2002-062323 | 2/2002 |
| JP | 2007-272413 | 10/2007 |
| JP | 2011-030106 | 2/2011 |
| JP | 2011-526191 | 10/2011 |
| JP | 2014-519352 A | 8/2014 |
| WO | WO2000074572 | 12/2000 |
| WO | 2006135520 A1 | 12/2006 |
| WO | 2007108914 A2 | 9/2007 |
| WO | WO2009144461 | 12/2009 |

(56) References Cited

FOREIGN PATENT DOCUMENTS

| WO | WO2009158601 | 12/2009 |
| WO | WO2010129026 | 11/2010 |
| WO | WO 2012140510 A2 | 10/2012 |
| WO | WO2013110001 | 7/2013 |
| WO | 2013/140744 A1 | 9/2013 |
| WO | 2014152374 A1 | 9/2014 |
| WO | 2016/036946 A1 | 3/2016 |

OTHER PUBLICATIONS

Griffiths et al., "Magnetic induction tomography. A measuring system for biological tissues," Ann N Y Acad Sci., 873:335-345, Apr. 20, 1999.

Wise et al., "The value of hypertonic mannitol solution in decreasing brain mass and lowering cerebro-spinal-fluid pressure," J Neurosurg., 19:1038-1043, Dec. 1962.

Bey et al., "Second impact syndrome," West J Emerg Med., 10(1):6-10, Feb. 2009.

Boody et al., "Accuracy in the measurement of compartment pressures: a comparison of three commonly used devices," J Bone Joint Surg Am., 87(11):2415-2422, Nov. 2005.

International Search Report & Written Opinon for PCT/US2016/069209, dated Jun. 26, 2017, 13 pages.

Sun et al., "Silent brain injury after cardiac surgery: a review: cognitive dysfunction and magnetic resonance imaging diffusion-weighted imaging findings," J Am Coll Cardiol., 60(9):791-797, Aug. 28, 2012.

Beehive Electronics Datasheet. 100 Series EMC Probes. Sebastopol, California. 4 pgs, Apr. 13, 2009.

Borchardt, "The Beginnings of Drug Therapy: Ancient Mesopotamian Medicine" (Abstract only), Drug News Perspect., 15(3):187-192, Apr. 2002.

González et al., "In Vivo Inductive Phase Shift Measurements to Detect Intraperitoneal Fluid," IEEE Trans Biomed Eng., 54(5):953-956, May 2007.

European Search Report and Written Opinion Application No. 13738728.8, dated Aug. 25, 2015, 5 pages.

Gonzales et al., "The detection of brain oedema with frequency-dependent phase shift electromagnetic induction," Physiol. Meas., 27(6): 539-552, Epub Apr. 7, 2006.

Gonzales et al., "Over-hydration detection in brain by magnetic induction spectroscopy", Journal of Physics: Conference Series, 224: 012123, 2010, 4 pages.

Gonzales et al., "The detection of brain ischaemia in rats by inductive phase shift spectroscopy," Physiol. Meas., 30(8): 809-819, Epub Jun. 30, 2009.

Gonzalez, et al., "Volumetric electromagnetic phase-shift spectroscopy of brain edema and hematoma," PLoS One, 8(5):e63223. May 14, 2013.

International Search Report & Written Opinion for PCT/US2013/022316, dated Apr. 30, 2013, 7 pages.

International Search Report & Written Opinion for PCT/US2015/048336, dated Dec. 8, 2015, 13 pages.

Len et al., "Cerebrovascular Reactivity Impairment After Sport-Induced Concussion", Official Journal of the American College of Sports Medicine, Clinical Sciences, Medicine & Science in Sports & Exercise by the American College of Sports Medicine, http://www.acsm-msse.org, pp. 2241-2248, 2011.

Xu et al. "Study of PSSMI for Cerebral Hemorrhage Detection: An Experimental Simulation," 2011 4th International Congress on Image and Signal Processing (CISP), IEEE, pp. 266-268, Oct. 15, 2011.

Roberts et al., "Mannitol for Acute Traumatic Brain Injury," The Cochrane Database of Systematic Reviews, Issue 2, Art No. CDOO 1049. DOI:10.1002/14651858. CD001049, The Cochrane Collaboration. Published by John Wiley & Sons, Ltd., pp. 1-7, Mar. 1, 2005.

Smith, "Signal and Noise Measurement Techniques Using Magnetic Field Probes," http://www.emcesd.com/pdf/emc99-w.pdf., IEEE 1999 EMC Symposium Proceedings, pp. 559-563, 1998.

Ullman, "Wireless Helmet Detects Brain Trauma," Baylor Innovations, 8(1): 14-15, Jun. 2014.

\* cited by examiner

DIFFERENTIATION OF FLUID VOLUME CHANGE

CROSS-REFERENCE TO RELATED APPLICATIONS

This application is a continuation-in-part of U.S. patent application Ser. No. 14/844,681, titled "Detection and Analysis of Spatially Varying Fluid Levels Using Magnetic Signals," filed Sep. 3, 2015, which issued as U.S. Pat. No. 10,743,815, on Aug. 18, 2020 which is a continuation-in-part of U.S. patent application Ser. No. 14/690,985, titled "Method for Detecting and Treating Variations in Fluid," filed Apr. 20, 2015, which issued as U.S. Pat. No. 10,335,054, on Jul. 2, 2019, which is a continuation of U.S. patent application Ser. No. 14/275,549, titled "Method for Detecting and Treating Variations of Fluid," filed May 12, 2014, now abandoned, which is a continuation of U.S. patent application Ser. No. 13/745,710, titled "Diagnostic Method for Detection of Fluid Changes Using Shielded Transmission Lines as Transmitters or Receivers," filed Jan. 18, 2013, and issued as U.S. Pat. No. 8,731,636, on May 20, 2014, which claims benefit of U.S. Provisional Patent Application Ser. No. 61/588,516, titled "Diagnostic Device for Detection of Fluid Changes in the Brain and Other Areas of the Body," filed Jan. 19, 2012.

TECHNICAL FIELD

This application is related to noninvasive, diagnostic, medical devices, systems and methods. More specifically, some embodiments of this disclosure relate to devices, systems and methods that use volumetric integral phase-shift spectroscopy ("VIPS") to monitor changes in fluids in the brain or other parts of the body. (VIPS may alternatively be referred to by other acronyms, such as magnetic induction phase-shift spectroscopy ("MIPS")).

BACKGROUND

In many different medical settings, it would be advantageous to be able to detect changes in bodily fluid composition and distribution as they occur, in a noninvasive manner. For example, it is often critical to monitor changes in intracranial fluid content or distribution in an intensive care unit patient. Standard of care for these patients includes invasive monitors that require drilling a hole in the cranium and inserting a probe, such as an intracranial pressure (ICP) monitor, or microdialysis or "licox" probes, for measuring chemical changes to the fluids in the brain. No continuous, noninvasive measurement techniques are currently commercially available for detecting cerebral fluid changes, such as those that occur with bleeding or edema. Furthermore, many brain injuries are not severe enough to warrant drilling a hole in the cranium for invasive monitoring. Thus, for many patients with brain injury, there is no continuous monitoring technology available to alert clinical staff when there is a potentially harmful increase in edema or bleeding. Instead, these patients are typically observed by nursing staff, employing a clinical neurological examination, and it is not until changes in the fluid composition or distribution in the brain cause observable brain function impairment that the physicians or nurses can react. In other words, there is no way currently available for monitoring intracranial fluid changes themselves, and thus the ability to compensate for such changes is limited.

VIPS has been previously proposed for diagnosis of brain fluid abnormalities. Patents have been awarded for proposed devices, and promising scientific studies of prototype devices are described in the literature. For example, Rubinsky et al. described the use of VIPS for this purpose, in U.S. Pat. Nos. 7,638,341, 7,910,374 and 8,101,421, the disclosures of which are hereby incorporated in their entirety herein (referred to herein as the "Rubinsky Patents"). Wyeth et al. described additional details of the use and design of VIPS devices in U.S. Pat. No. 8,731,636, which is hereby incorporated in its entirety herein. However, no practical, mass-produced medical device based on VIPS technology has yet emerged, to provide clinicians specializing in brain treatment or other areas of medicine the promised benefits of such a device.

Ideally, a medical device solution would provide a VIPS system with improved performance, usability and manufacturability, such that it could be used for noninvasive fluid change detection in the brain and/or other areas of the body. The embodiments described herein endeavor to address at least some of these objectives.

BRIEF SUMMARY

In one aspect, a method for measuring a fluid volume in a patient's brain to help determine the presence an occlusion of a blood vessel supplying the brain may involve: securing a volumetric integral phase-shift spectroscopy (VIPS) device to the patient's head; measuring a fluid volume with the VIPS device; and determining, using the measured fluid volume, whether an occlusion of a blood vessel supplying the brain is present. In some embodiments, the method may further involve determining in which hemisphere of the brain the occlusion is located. In some embodiments, measuring the fluid volume may involve comparing a first fluid volume in one hemisphere of the brain with a second fluid volume in the other hemisphere of the brain, and determining whether the occlusion is present may involve comparing the first fluid volume with the second fluid volume. Some embodiments may also involve determining in which hemisphere of the brain the occlusion is located, based on the comparison of the two fluid volumes.

In some embodiments, measuring the fluid volume may involve monitoring the fluid volume over time to detect changes in the fluid volume. Optionally, the method may also involve measuring the fluid volume after a procedure is performed to remove the occlusion. One example of a type of occlusion that may be detected using this method is a large vessel occlusion.

In another aspect, a method for monitoring fluid volume changes in a patient's brain after treatment of an occlusion of a blood vessel supplying the brain may involve: securing a volumetric integral phase-shift spectroscopy (VIPS) device to the patient's head; measuring a fluid volume with the VIPS device; and providing data regarding the measured fluid volume to a user to help the user determine if the treatment was successful. In some embodiments, measuring the fluid volume may involve measuring a first fluid volume before the treatment is performed and measuring at least a second fluid volume after the treatment is performed. Optionally, such an embodiment may also involve comparing the first fluid volume with the second fluid volume to detect a change between the first and second fluid volumes.

In an alternative embodiment, measuring the fluid volume may involve comparing a first fluid volume in one hemisphere of the brain with a second fluid volume in the other hemisphere of the brain. Such an embodiment may optionally also involve comparing the first fluid volume with the second fluid volume. The method may also optionally involve determining in which hemisphere of the brain the occlusion is located, based on the comparison of the two fluid volumes. In some embodiments, measuring the fluid volume involves monitoring the fluid volume over time to detect changes in the fluid volume.

In another aspect, a volumetric integral phase-shift spectroscopy (VIPS) device for measuring a fluid volume in a patient's brain to help determine the presence an occlusion of a blood vessel supplying the brain may include: a frame comprising a housing; circuitry housed within the housing; at least one receiver housed within the housing; two wrap-around ends, configured to wrap around the back of a patient's head and over the ears; two transmitters, wherein one transmitter is housed in one of the two wrap-around ends, and the other transmitter is housed in the other of the two wrap-around ends; two holding arms extending from the frame to contact the patient's ears and help support the device on the patient's head; and a nosepiece configured to rest on the patient's nose to help support the device on the patient's head. In some embodiments, the device may be configured to detect at least two different fluid volumes. One of the fluid volumes may be a first fluid volume in a right hemisphere of the brain, and another of the fluid volumes may be a second fluid volume in a left hemisphere of the brain.

In one embodiment, the present disclosure includes a device for detecting spatial differences in fluid volume changes in a tissue of a patient. The device includes a support structure for securing the device to a body part of a patient, a processing element operably connected to the support structure, a wireless networking interface operably connected to the support structure and in communication with the processing element and an external computing device via a wireless network. The device also includes first, second, and third transmission modules, each of the modules are connected to the support structure and are in communication with the processing element. The second and third transmission modules are spatially separated from one another relative to the tissue of the patient, and the first transmission module is opposed to the second and third transmission modules, so as to transmit signals form the modules as they are transmitted through the tissue. When activated, the first transmission module transmits a first time varying magnetic field through the tissue of the patient, and the second and third transmission modules receive first and second versions, respectively, of the first magnetic field and transmit a first received magnetic field data corresponding to the first and second versions to the processing element. The processing element provides transmission data corresponding to the first received magnetic field data to the wireless networking interface, which in turn transmits the transmission data wirelessly to the external computing device. In another implementation, the first transmission module may be configured to receive first and second time varying fields transmitted by the second and third transmission modules, respectively.

In yet another embodiment, the present disclosure includes a method for detecting symmetry in fluid volumes in a tissue of a patient. The method includes securing a device, including a receiver, a first transmitter, and a second transmitter on the patient's head, such that the first transmitter and the second transmitter are spatially separated from one another and the receiver is positioned to be in communication with the first transmitter and the second transmitter via a transmission pathway through the tissue. The method further includes transmitting a first time varying magnetic field from the first transmitter, transmitting a second time varying magnetic field from the second transmitter, receiving a first received field and a second received with the receiver, analyzing at least one transmission characteristic with a processing element, determining with the processing element that the first received field corresponding to the first time varying magnetic field and the second received field corresponds to the second time varying magnetic field, determining with the processing element a first phase shift between the first time varying magnetic field and the first received field, determining with the processing element a second phase shift between the second time varying magnetic field and the second received field and determining with the processing element a change in fluid in the tissue over a period of time based on the determined first and second phase shifts.

In yet another embodiment, the present disclosure includes a method for detecting variations in fluid volumes in a patient. The method includes attaching a headset to the patient, the headset including a support band for securing the headset to a head of the patient, a processing element coupled to the support band and configured to transfer data wirelessly to an external computer, and multiple transmitter receiver components operably connected to the support band at discrete locations. The method further includes activating the headset to take one or more fluid volume readings within the head of the patient, wirelessly transmitting the fluid data corresponding to the one or more fluid volume readings from the processing element to the external computer, and analyzing the fluid data with the external computer.

In another aspect of the present disclosure, a method for detecting evidence of a stroke in a patient may involve securing a volumetric integral phase-shift spectroscopy (VIPS) device to the patient's head, transmitting a first signal from a first transmitter of the VIPS device through a left hemisphere of the patient's brain to a receiver of the VIPS device, transmitting a second signal from a second transmitter of the VIPS device through a right hemisphere of the patient's brain to the receiver, and detecting the evidence of the stroke, with the VIPS device.

In some embodiments, the method may also include detecting the evidence comprises detecting a difference between the right hemisphere and the left hemisphere. Optionally, the method may involve determining in which hemisphere of the patient's brain the stroke occurred. In some embodiments, detecting the difference between the left hemisphere and the right hemisphere may involve comparing a first fluid volume in the left hemisphere of the brain with a second fluid volume in the right hemisphere of the brain. Optionally, some embodiments may further involve correlating the detected difference to a volumetric unit of measure by using a CT image as a transfer standard. In some embodiments, detecting the difference may involve monitoring fluid volumes in the left hemisphere and the right hemisphere over time to detect changes in the fluid volumes.

Optionally, the method may involve repeating the steps after a procedure is performed to treat the stroke. In some embodiments, the evidence may include a measurement of a volume in the patient's head that is within a range indicative of an abnormality. For example, the volume may be a fluid volume, a solid volume, a tissue volume, a bulk volume or the like.

In yet another aspect of the present disclosure, a method for detecting evidence of an abnormality in a patient's brain may involve securing a volumetric integral phase-shift spectroscopy (VIPS) device to the patient's head, transmitting a first signal from a first transmitter of the VIPS device through a left hemisphere of the patient's brain to a receiver of the VIPS device, transmitting a second signal from a second transmitter of the VIPS device through a right hemisphere of the patient's brain to the receiver, and detecting the evidence of the abnormality, with the VIPS device.

In some embodiments, detecting the evidence involves detecting a difference between the right hemisphere and the left hemisphere. Some embodiments may further involve determining in which hemisphere of the patient's brain the abnormality has occurred. In some embodiments, detecting the difference between the left hemisphere and the right hemisphere involves comparing a first fluid volume in the left hemisphere of the brain with a second fluid volume in the right hemisphere of the brain. In some embodiments, detecting the evidence may involve comparing a measurement by the VIPS device with a measurement or a range of measurements defined as normal.

In another aspect of the disclosure, a method for detecting a change in a fluid volume in a head of a patient may involve securing a volumetric integral phase-shift spectroscopy (VIPS) device to the patient's head, measuring a fluid volume with the VIPS device, and measuring a cyclical change in amplitude of the fluid volume. The method may also involve measuring the cyclical change in amplitude over time. The method may also involve measuring a rate of the cyclical change in amplitude over time.

In some embodiments, the method may also involve determining that an event has occurred in the brain. In some embodiments, the method may also involve determining a hemisphere of the brain in which the event has occurred. Measuring the fluid volume may involve comparing a first fluid volume in one hemisphere of the brain with a second fluid volume in the other hemisphere of the brain, where determining the hemisphere involves comparing the first fluid volume with the second fluid volume. In some embodiments, the patient may be receiving cardiopulmonary resuscitation, and the method may further include determining a rate of chest compressions based on the measurements.

These and other aspects and embodiments are described more fully below, in reference to the attached drawing figures.

DETAILED DESCRIPTION

Certain details are set forth below to provide a sufficient understanding of certain embodiments of the present disclosure. However, some embodiments of the disclosure may be practiced without these particular details. Moreover, the particular embodiments of the present disclosure are provided by way of example and should not be used to limit the scope of this disclosure to those particular embodiments. In some instances, well-known circuits, control signals, timing protocols, and software operations have not been shown in detail, in order to avoid unnecessarily complicating the description.

Overall System Architecture

Figure 1:
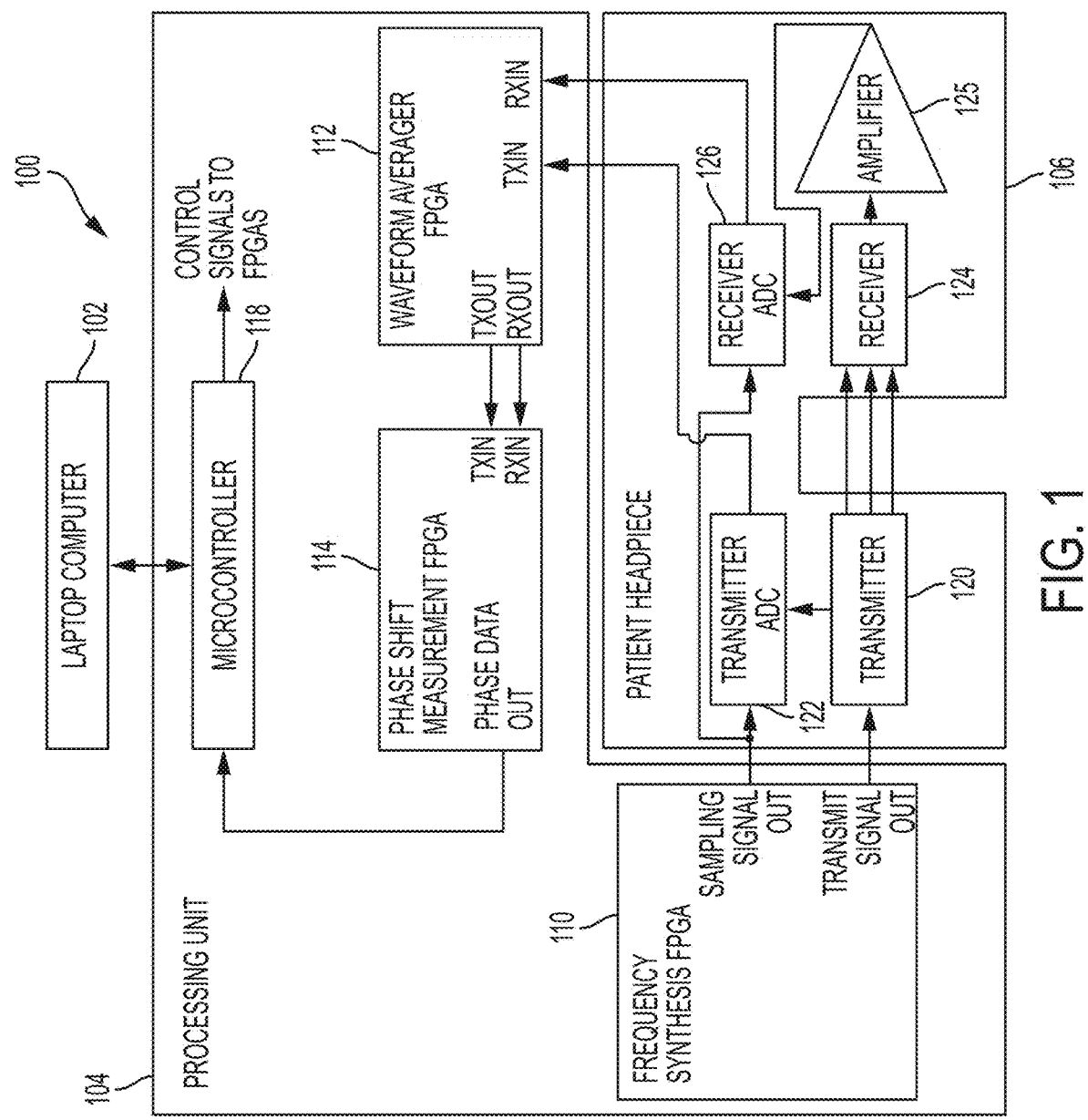
FIG. 1 is a block diagram of a system for monitoring fluid changes in the body, according to one embodiment.

FIG. 1 is a block diagram of one embodiment of a system 100 that may be used to detect fluid changes in a human brain. Although this description often focuses on use of the system 100 for detecting fluid changes in the brain, this embodiment of the system 100 or alternative embodiments may be used for detecting/monitoring fluid changes in any other part of the body. Therefore, the exemplary description provided herein that is directed toward the brain should not be interpreted as limiting the scope of the invention as it is set forth in the claims.

The system 100 may include a laptop computer 102 or other computing device, a processing unit 104, and a patient headpiece 106 in some examples. The system 100 may be controlled, for example, by a windows-based labview language program running on the laptop computer 102. The program generates a graphical user interface (GUI) that is displayed on the screen of the laptop 102. The clinician who operates the system 100 may initiate monitoring by mouse control after placing the headpiece 106 on the patient, which may be similar to an elastic headband or bandage. After initiation of monitoring, the program may run unattended as it logs the phase shift data on the laptop 102 and applies the appropriate methods to generate alarms and suggested corrective actions to a clinician.

The laptop 10, which may be an external computer relative to the patient headpiece 106, may have a USB serial link to the processing unit 104. This USB link may be electrically isolated to conform to applicable medical device requirements. The processing unit 104 may derive power from a standard universal AC line power connection consistent with international standards. There may be a medical grade low-voltage DC power supply to power all of the processing unit's 104 internal electronics that meets applicable standards for patient isolation, line to neutral, chassis, and patient leakage as well as earth to ground continuity, EMI susceptibility and emissions, and other standard medical device requirements.

The laptop 102 may initiate phase shift data collection and log the data in files on the laptop's 102 hard drive along with other pertinent data and status information.

The GUI on the laptop 102 may control the operation of the system 100, and may include controls and status indications that guide the clinician through installation of the patient headpiece 106 and a preliminary self-test of the entire system 100. If the self-test passes, the clinician is instructed to initiate monitoring. During monitoring, the phase shift angle versus frequency data is collected from the USB interface and appropriate status and alert methods are applied to the data. The clinician may be informed if additional actions or emergency responses are indicated. The phase shift versus frequency data and additional status information is logged in the laptop 102 for later reference. A "sanity check" of the data and other built-in-test features may run continuously in the background, and if a fault is encountered, various levels of severity will generate warnings or interrupt operation of the system 100.

The architecture of hardware and firmware in the processing unit 104 and the patient headpiece 106 may be optimized to achieve the desired phase measurement accuracy and stability while using a minimum number of custom electronics components in some examples and as illustrated in FIG. 1. For example, in one embodiment, and with reference to FIG. 1, the system 100 may comprise several highly integrated miniaturized off-the-shelf components. The system 100 may include three field programmable gate arrays (FPGAs) 110, 112, 114 in the processing unit 104, the three FPGAs being programmed with appropriate firmware. One FPGA 110 may synthesize a time-varying signal to be provided to a transmitter (transmitter may be alternatively be referred to by emitter) 120 to generate a magnetic field, the second FPGA 112 may collect and average digital samples of transmitted and received magnetic fields, and the third FPGA 114 may measure the phase shift between the transmitted and received signals representative of the transmitted and received magnetic fields.

A microcontroller 118 may also be included in the processing unit 104, and may supervise the actions of the three FPGAs 110, 112, 114 and communicate with the laptop 102 (e.g., by transferring phase data results). The microcontroller 118 may provide an interface between the external laptop computer 102 (via an electrically isolated USB interface) and the FPGAs 110, 112, 114 used for real time signal processing of the data from the headpiece 106. The microcontroller 118 may also perform other miscellaneous functions such as the interface to basic user controls including power-on, initiation of data collection, setup of the frequency synthesizer 110, internal temperature monitoring, power supply monitoring, and other system status monitoring and fault detection tasks.

The processing unit 104 may in some examples be fabricated from larger, integrated components. In one embodiment, the processing unit 104 may include an off-the-shelf electronic signal generator, such as a Techtronix Arbitrary Waveform Generator model 3252, and a digital oscilloscope such as LeCroy Model 44xi. Conversely, processing unit 104 could be integrated into a single ARM processor.

The architecture of the system 100 illustrated in FIG. 1 may be relatively flexible, allowing improvements in all phases of the data collection, data processing, and data interpretation (e.g., clinical alerts) to be made through relatively simple software or firmware modifications. The FPGAs 110, 112, 114 may effectively function as parallel processors to make data collection and processing proceed in near real time. The quantity of phase data transmitted via the microcontroller 118 to the laptop 102 and archived for later reference may thus be reduced, thereby requiring less computation time on the laptop 102 for processing the data. This may in turn free up the laptop 102 for checking data consistency and applying methods required for alerting clinicians to the need for corrective actions.

Although the processing unit 104 in FIG. 1 has been illustrated and described as a relatively flexible embodiment, in other examples the diagnostic system 100 may be an embedded system with custom electronics components specially designed for use in the diagnostic system 100. For example, one or more analog to digital (A to D) converters may be located in the processing unit 104, which may be physically distinct and separate from the headpiece 106, or which may be integral with the headpiece 106 (e.g., the headpiece 106 may, in a custom system 100, include all of the electronics and processing equipment needed to capture and process phase shift information). Also, the functions executed by the three FPGAs may be combined into one FPGA. In general, any suitable architecture may be used.

Referring again back to FIG. 1, the system 100 may also include a headpiece 106 with transmission modules, such as one or more transmitters 120 and one or more receivers 124, the details of which are explained in more detail below. In one example, the headpiece 106 includes a single transmitter 120 and a single receiver 124, whereas in other examples, the headpiece 106 includes several transmitters 120 and/or several receivers 124. For example, the headpiece 106 may include one transmitter 120 and two receivers 124. If multiple receivers 124 are placed at different positions over a patient's head, they may allow a clinician to triangulate the location of a fluid change (e.g., intracerebral bleeding from a blood vessel or tumor) and/or image the biological impedance of a patient's brain. In other examples, the headpiece 106 may include multiple transmitters 120, which may produce magnetic fields at different or similar frequencies. If different frequencies are used, a single or multiple receivers 124 may be able to distinguish among the several transmitted frequencies in order to, for example, further distinguish the type of fluid change. As discussed in more detail below, other types of transmission characteristics, such as variations in time transmission, wave shape, frequency, attenuation, amplitude, and/or additional waves may be used to identify a particular transmitter for a particular signal.

In some examples, in addition to the receiver 124 positioned elsewhere on the patient's head, an additional receiver may be positioned on the same side of the patient's head as the transmitter 120 (e.g., the receiver may be concentric within or may circumscribe the transmitter 120, or may be positioned in a separate plane from the transmitter 120) in order to obtain a measurement of the transmitted magnetic field from the transmitter (not shown in FIG. 1). In other examples, the emitted magnetic field may be sampled from the transmitter 120 in another fashion, such as by measuring the current and/or voltage present on the transmitter 120. In some examples, and with reference to FIG. 1, the patient headpiece 106 includes A to D converters 122, 126 for one or more of the transmitter(s) 120 and/or receiver(s) 124 proximate the respective transmitter(s) 120 and/or receiver(s) 124 themselves—for example, A to D converters may be positioned on the same printed circuit board as the respective transmitters 120 or receivers 124 in some examples.

In other examples, however, the analog signals are not converted into digital signals until after being passed through one or more coaxial cables (or other transmission lines) connected to a separate processing unit (e.g., the processing unit 104 shown in FIG. 1). In these examples, various techniques may be employed to reduce cross-coupling between, for example, a coaxial cable carrying a signal indicative of the transmitted magnetic field from the transmitter 120 and a coaxial cable carrying a signal indicative of the measured magnetic field from the receiver 124. For example, a relatively flexible RF-316 double shielded cable may be used to increase the isolation between the two cables, or, in other examples, triple shielded cables may be used. As another option, highly flexible PVC or silicone tubing may be provided around the coaxial cable from the receiver 124 and/or transmitter 120.

Figure 1A:
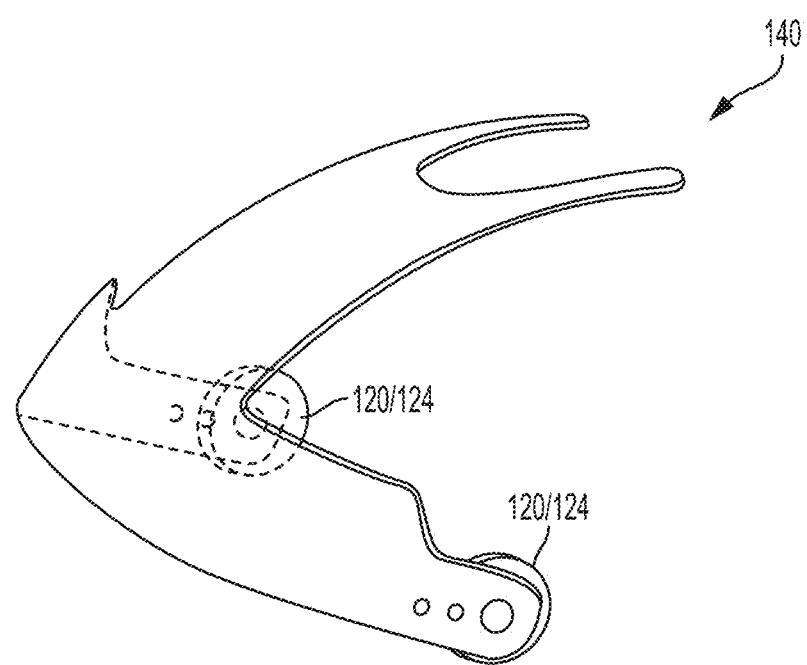
FIG. 1A is a perspective view of a patient headpiece for use in the system of FIG. 1, according to one embodiment.

Referring again to the headpiece 106 illustrated in FIG. 1, for repeatable readings, it may be important for the transmitter 120 and receiver 124 to not move during operation of the system 100 because such movement may introduce an error in the phase shift measurement. In order to overcome such errors, the transmitter 120 and receiver 124 may be mounted in a rigid manner in some examples, for example in an apparatus that resembles a helmet 140, one example of which is illustrated as FIG. 1A. The helmet 140 may provide the necessary support and rigidity to ensure that the transmitter 120 and receiver 124 remain fixed relative to each other and relative to the patient's head. However, such a helmet 140 may be uncomfortable or impractical to use on a patient while they are lying down. Also, it may not be practical for a patient to wear the helmet 140 for several days as may be desirable in some clinical situations.

Figure 1B:
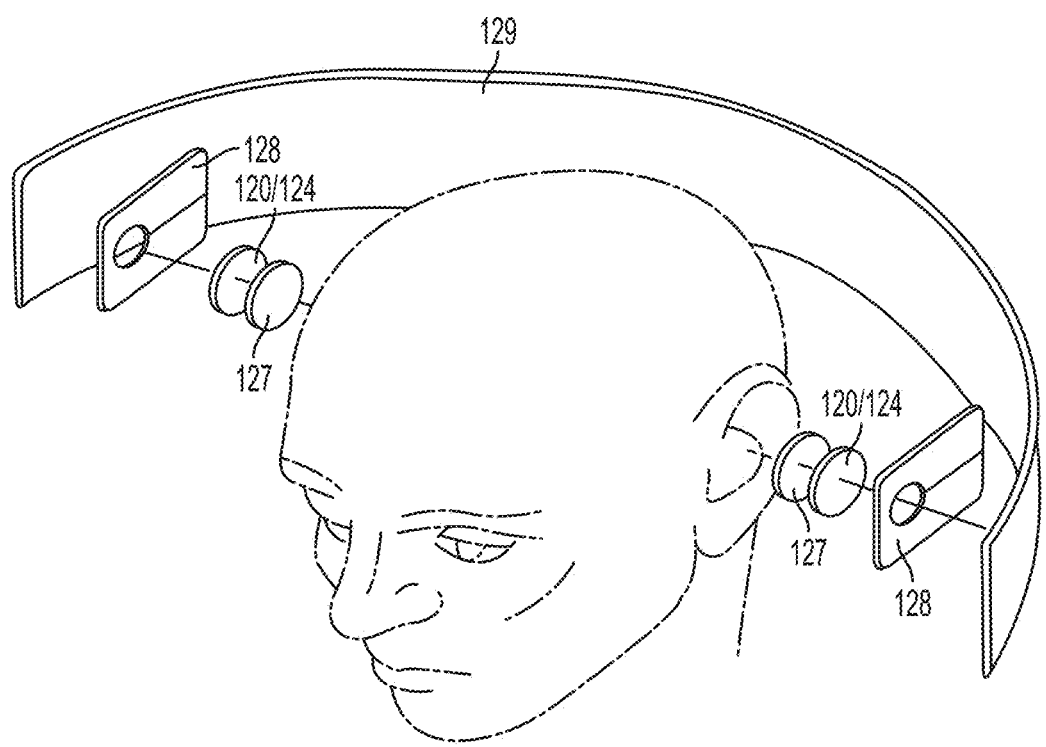
FIG. 1B is a perspective exploded view of a patient headpiece for use in the system of FIG. 1, according to an alternative embodiment.

Accordingly, in an alternate embodiment, and with reference to FIG. 1B, the transmitter 120 and receiver 124 are held against the head of the patient using a headset 129, such as an elastic band 129. The transmitter 120 and receiver 124 may be mounted on the headset 129, for example, by securing them inside a pocket of the headset 129, or using stitches, rivets or other fasteners. The transmitter 120 and receiver 124 may be spaced at a fixed distance from the surface of the skin by incorporating a non-conductive spacer material 127, such as plastic or fabric. The spacers 127 can serve the purpose of maintaining a fixed distance between the transmitter 120 and receiver 124 from the skin in order to, for example, reduce variability of the capacitance between the transmitter 120/receiver 124 and the skin. The spacers 127 may be, for example plastic acrylic disks in some embodiments. Rubber, medical adhesive, or other material may also or alternatively be used for the spacers 127, and may be placed at the skin interface surface of the transmitter 120 and receiver 124 to aid in keeping them from moving during use.

The headset 129 may be placed on the patient's head across the forehead and around the back of the head in some embodiments; or a different band or other device can be placed in other configurations, including around a patient's chest, arm or leg. In other words, any suitable positioning device may be used to appropriately position the transmitter 120 and receiver 124 proximate the area of the patient's body under investigation, of which the headsets 106, 129 and headbands 129 described herein are merely examples. Additional features such as a chin strap or a connection over the top of the head can be added to the headset 129 to provide additional stability and to provide features on which to mount additional transmitters 120 or receivers 124. Since the patient will often be lying on a pillow, a convenient location for electrical components and for cable terminations might be the top of the head. For example, a bridge from a point near each ear may be created so that the electronics can be mounted at the top of the head, away from the surfaces that the patient may lie on. Low-profile components that are lightweight may be used so as to maximize comfort and minimize the tendency of the headset to move on the patient's head once in place.

In the headset 129 design, a headband 129 may be made of elastic, rubber, acrylic, latex or other flexible material, and may be elastic or inelastic. The headset 129 may be fabricated from inexpensive materials so the headset can be a disposable component of the system. Alternatively, the headset 129 may be reusable. If it is reusable, the band 129 may be washable so that it can be cleaned between patients, or cleaned periodically for the same patient. Washable materials may include plastic, rubber, silicone, fabric, or other materials. The headpiece 106 may also include mounting means for securing the electronic components and to route the cables to keep them from getting in the way of the patient or the clinical staff.

In some embodiments, including those where a headband 129 is used, in order to reduce the relative motion between the transmitter 120/receiver 124 and the patient, one or more stabilizers 128 may be used. Stabilizers 128 may be custom-molded to the patient's body to hold the transmitter 120 and/or receiver 124 in place. As one example of a stabilizer 128, trained clinicians may install the transmitter 120/receiver 124 using low-melting-point plastic that is similar to orthopedic casts made from the same material. Other custom-shapeable materials and methods may be used, such as materials which polymerize over time, or with activation by heat or chemical reaction such as materials used for making orthopedic casts or splints.

With reference now to the exploded view of FIG. 1B, the operation of one embodiment of using a headset 129 will be described, although it will be understood that similar bands 129 may be used to monitor fluid change in other parts of the body, such as a bandage wrapped around a leg or an arm. Each transmitter 120/receiver 124 may first be coupled to a respective spacer 127 by, for example, a screw or other fastener such as glue. The transmitter 120 and respective spacer 127 may then be positioned on a patient's head, and the stabilizer 128 may be positioned around the transmitter 120/spacer 127 in order to stabilize the transmitter and help prevent movement. The stabilizer 128 may need to be soaked in water or otherwise prepared for application prior to positioning it around the transmitter 120/spacer 127. Once the stabilizer 128 secures the transmitter 120/spacer 127, another stabilizer 128 may similarly be used to stabilize the receiver 124 and spacer 127 in a similar manner. The stabilizers 128 may solidify or dry out to perform the stabilizing function. Then, a headset such as a headband 129 may be wrapped around the stabilizers 128 and transmitter 120/spacer 127 and the receiver 124/spacer 127. In some embodiments, however, no stabilizers may be used, and the headband 129 may instead be used to directly position the receiver 124/spacer 127 and the transmitter 120/spacer 128 on the patient's head. In still other embodiments, and as mentioned above, the headband 129 may include pockets for the transmitter 120 and receiver 124, with the headband 129 material itself acting as a spacer. Also, in some embodiments, the headband 129 may have non-slip material applied to an interior side of the headband 129 to help prevent slippage of the headband 129 on the patient's head.

Figure 8:
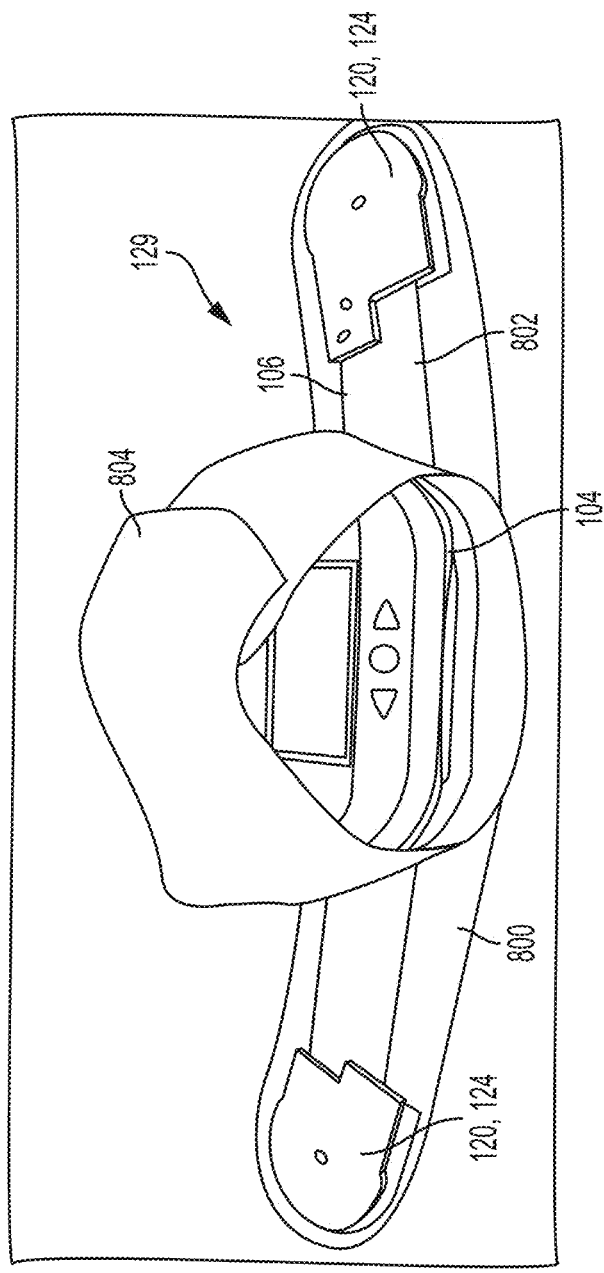
FIG. 8 is an isometric view of a system for monitoring fluid changes including a temporary stabilizer, according to one embodiment.

Other examples of the headset 129 may be used as well. FIG. 8 illustrates an isometric view of an example of the headset 129. In this embodiment, the headset 129 may be substantially similar to the headset 129 shown in FIG. 1B. However, in this example, a stabilizer 800 may be included with the headset 129. Additionally, the headset 129 may include a flexible circuit 802 or other wiring mechanism that may extend between the processing unit 104 and the transmitters and receivers 120, 124. The headset 129 may also include a securing element 804 such as a headband, elastic, or the like, which may be flexed and/or stretched to secure the headset 129 around a patient's head.

The stabilizer 800 temporarily secures the headset 129 on a user's head (or other desired location), but may allow the headset 129 to be removed when monitoring is no longer desired. The stabilizer 800 may generally be a skin compatible adhesive. The stabilizer 800 may be two-sided adhesive where one side may be secured to the headset 129 (such as to the flexible circuit 802 or securing element 804) and the other side may be secured to the patient's head. As another example, stabilizer 800 may be adhesive such as glue or another similar fluid or gel with adhesive properties. As a specific example, the stabilizer 800 may be hydrogel.

In embodiments including the stabilizer 800, the stabilizer 800 stabilizes and locks the various components of the headset 129 onto a specific position on the patient's body. This helps to ensure accurate readings, as the electronics (e.g., transmitters and receivers) and circuit 802 may remain in substantially the same orientations and positions, even if the patient moves. Further, the stabilizer 800 may further help to prevent distortion of the electronics, as the flexible extensions of the transmitter and receiver (e.g., the flex circuit 802) can be shaped so as to curve or wrap around one dimension of the patient's head (or other monitored area), but do not substantially flex or stretch in the other dimension. As one example, the lateral positions of the transmitter and receiver 120, 124 (i.e., front to back) and the flexible circuit 802 may remain stable when pressed against the surface of a patient's head.

Various embodiments include mechanical mechanisms for determining correct placement, alignment, and attachment to a specific position on the patient's body. For example, the helmet 140 in FIG. 1A, the headband 129 in FIG. 1B, the headset 906 of FIG. 9, and the headset 950 of FIG. 11. These mechanisms help ensure accuracy and repeatability of the placements, which in turn helps to ensure the accuracy and precision of the readings. Further improvements for mechanical stability and repeatability could be enhanced with sensors to detect and monitor a point of contact or series of contacts to the patient's body. For example, sensors could be placed on arms 962 of headset 950 of FIG. 11 such that they detect when the arms 962 are in contact with a location where the scalp meets the ear of the patient. Additionally or alternatively, a sensor could be located to detect when the backside of the lenses 960 or top internal edge of the frame is at the right location to the forehead. Furthermore, the sensor or sensors could monitor the continued optimal placement of the headset during a measurement sequence. If at any time the headset moves away from the desired position, a sensor or sensors would send a signal to processing unit 104, which could in turn inform the user to correct the headset placement and or identify the measured data as non-ideal due to placement. A non-exhaustive list of the types of sensors that could be used in these embodiments include impedance, capacitive, conductive, optical, thermal, and distance.

Figure 9:
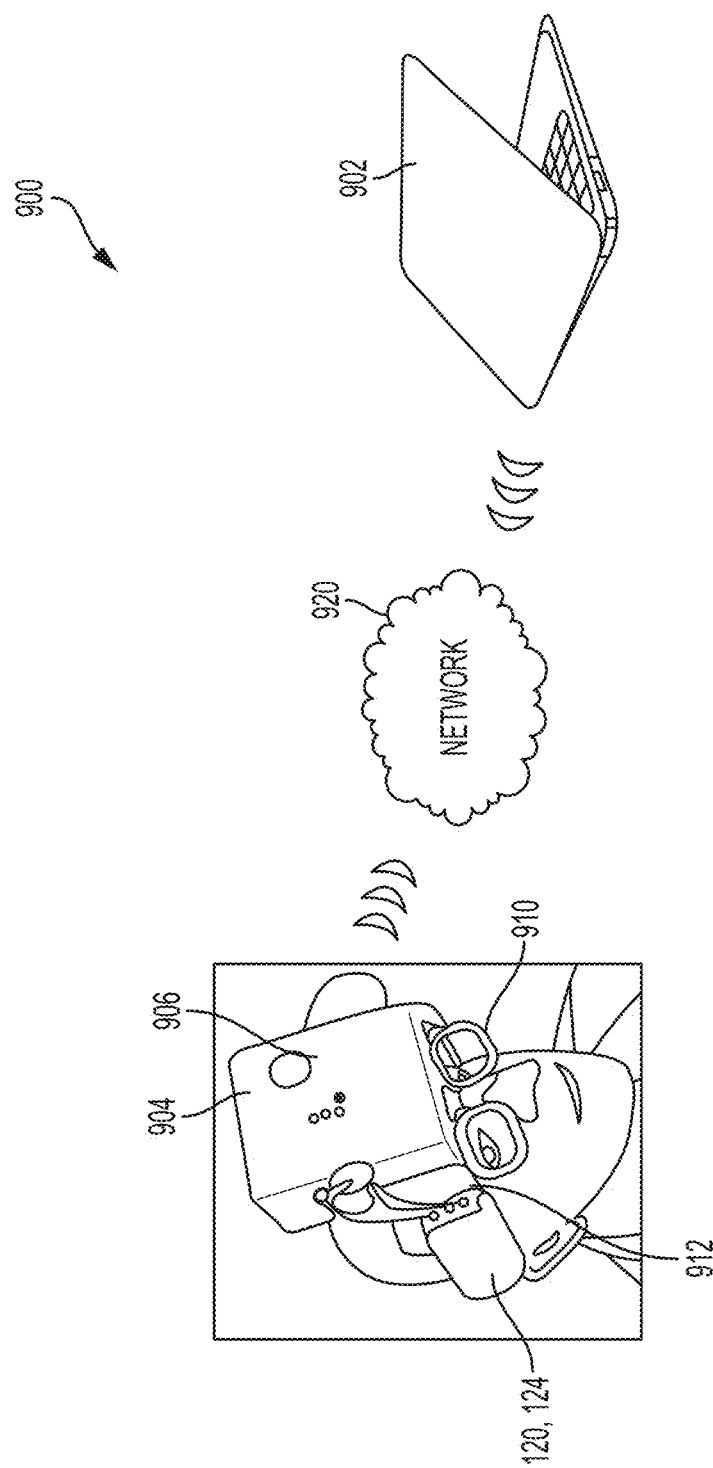
FIG. 9 is a system diagram for a system for monitoring fluid changes in a body, according to an alternative embodiment.
Figure 10:
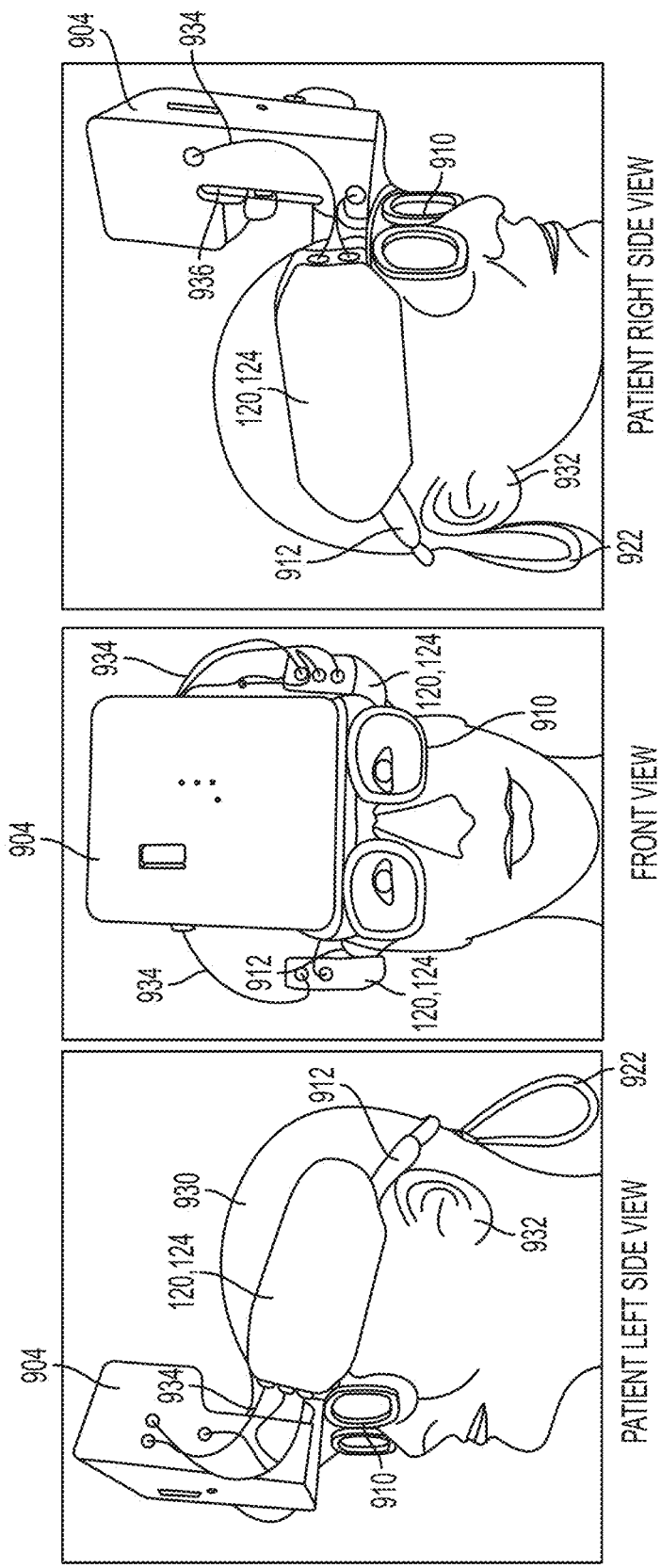
FIG. 10A is a left isometric view of a patient wearing the headpiece of the system of FIG. 9.
FIG. 10B is a front elevation view of the patient wearing the headpiece of FIG. 10A.
FIG. 10C is a right isometric view of a patient wearing the headpiece of FIG. 10A.

Another example of a system for detecting fluid volumes in a body will now be discussed. FIG. 9 is a diagram of a system 900 for detecting fluid volumes in a body. FIGS. 10A-10C illustrate various views of a patient wearing a headset 906 of the system 900. With reference to FIGS. 9-10C, the system 900 may include a headset 906 or support structure, a processing unit 104 having a network/communication interface for communicating with one or more external devices, one or more transmitters/receivers 124, 124, and a computing device 902. The computing device 902 may be in communication with the headset 906 and/or the processing unit 904 via a network 920. The network 920 may be, for example, WiFi, Bluetooth, wireless, or the like, and in many embodiments may be wireless to allow data to be transmitted from the processing unit 904 and headset 906 to the computing device 902 without cables, or the like. In these embodiments, the computing device 902 may be external from the headset 906, in that the computing device may be a standalone device that is in communication with the headset 906 via a wireless communication pathway. In other embodiments, the networking interface may be in communication via one or more wired pathways to the external computer and/or network.

The computing device 902 may be substantially similar to the computer 102 of FIG. 1. In some embodiments, the computing device 902 may be portable, to allow a treating physician to more easily transport the computing device 902 between different patients. However, in embodiments where portability may not be needed, the computing device 902 may be substantially any other type of computer, such as, but not limited to, a server, desktop computer, work station, or the like. It should be noted that the computing device 902, the processing unit 904, and/or headset 906 may include a networking interface component that provides a communication pathway to the network 920 from each respective device.

With reference to FIGS. 10A-10C, the headset 906 will now be discussed in more detail. The headset 906 in this example includes the processing unit 904 and the transmitters/receivers 120, 124. The integration of the processing unit 904 and transmitters/receivers 120, 124 onto a signal device allows the sensing unit to be more portable, easier to position on a patient, and enhances the mobility of the patient while the patient is wearing the device. Additionally, as discussed in more detail above, in embodiments where the processing unit 904 may do a substantial portion of the processing of the data close to the transmitters/receivers 120, 124, the risk of errors is reduced and the signal to noise ratio may also be reduced.

In one embodiment, the headset 906 includes a front support structure or frame 910 that defines the front of the sensing device. The front support structure 910 may support the processing unit 904 and define a frame for two lenses, e.g., for the left and right eyes of the patient. In embodiments where lenses are not required, such as when the patient does not need to wear glasses or have other eye protection, the lenses may be omitted to provide clarity for a user. The front support structure 910 may be varied as desired based on the size and structure of the processing unit 904.

With continued reference to FIGS. 10A-10C, the headset 906 may also include two arms 912 that extend from each end of the front support structure 910. The arms 912 are configured to wrap around a patient's head 930 and be supported above and/or on the patient's ears 912. The arms 912 may include contoured portions that better fit a patient's head 930 and/or ears 912 and that may further assist in retaining the device in position on the patient's head 930. The headset 906 may be adjustable and in some embodiments may include a securing strap 922 connected to the ends of each arm 912. The securing strap 922 is configured to tighten around the head 930 of the patient and secure the headset 906 in position. For example, a fastener or other device may selectively adjust the length of the securing strap 922 and assist in securing it around the head 930.

As discussed above, in this example the headset 906 is configured to be portable and the transmission modules, e.g., the transmitters/receivers 120, 124, are connected to the headset 906. In one example, such as the one shown in FIGS. 10A-10C, the transmitters/receivers 120, 124 may be connected to the arms 912 of the frame so that when the headset 906 is positioned on the patient's head 930, the transmitters and receivers 120, 124 will be positioned opposed to one another and oriented to receive and transmit signals through the user's head 930. The transmitters and receivers are configured to be in communication with one another and positioned so as to transmit or receive, respectively, signals to the corresponding device.

The transmitters/receivers 120, 124 or transmission modules may be in communication with and receive power from the processing unit 904. For example, a plurality of connection wires 934 may extend from the processing unit 904 and electrically connect the transmitters/receivers 120, 124 to the processing unit 904. The connection wires 934 may transmit power from a power source, such as a battery received within the battery slot 936 on the processing unit 904, along with data and/or signals from the processing unit 904. Additionally, the transmitters and receivers 120, 124 may transmit data to the processing unit 904, which may then transmit the data to the computing device 902. For example, the receivers 124 may transmit the received signals to the processing unit 904, which may then process the signals and transmit the data to the computing device 902 via the network 920.

Figure 11:
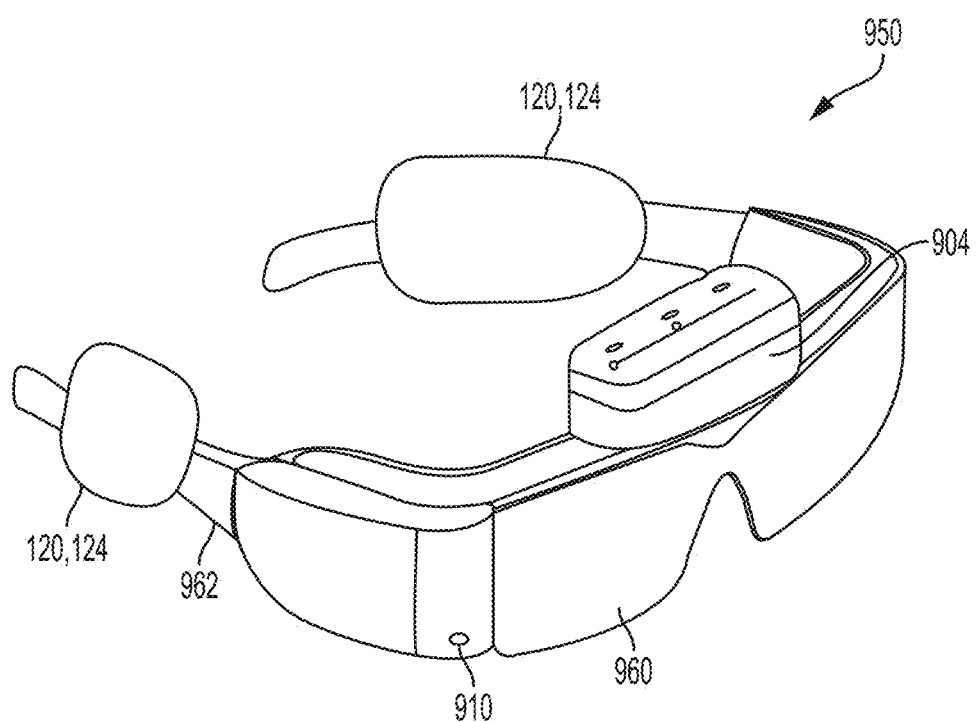
FIG. 11 is a front isometric view of a system for monitoring fluid changes in a body, according to another embodiment.

It should be understood that the arrangement and configuration of the headset 906 and processing unit 904 may be varied as desired. For example, in another example, the communication wires 934 may be omitted or incorporated into the frame or support structure of the headset 906. FIG. 11 is an isometric view of another example of the headset 906. With reference to FIG. 11, in this example, the headset 950 may be substantially similar to the headset 906 illustrated in FIGS. 10A-10C, but the communication wires 934 may be incorporated into the material and/or structure of the frame 910. Additionally, in this example, the headset 920 may include lenses 960 in the front support structure that may be modified based on the needs of the patient. The arms 962 of the headset 950 may extend from each end of the frame 910 and be configured to support the transmitters/receivers 120, 124 thereon. Additionally, in this example a third transmitter/receiver 120,124 could be configured on the backside of 904, adjacent to the forehead. As can be appreciated, the processing unit 904 may be smaller and centered on the frame 910, which provides better mobility for the patient while wearing the headset 906. Also, as the processing unit 904 is significantly smaller, it may be better able to remain in position and more accurately transmit data to and from the computing device 902 and/or transmitters/receivers 120, 124.

In some embodiments, the processing element 904 or unit is configured to provide transmission data corresponding to one or more of the received magnetic field data as received by the transmitters/receivers to the networking interface, which in turn transmits the transmission data to the external computing device 902. In these embodiments, the processing element 904 may convert the analog data as received from the transmitters and receivers into digital data before sending the data to the external computing device 902. This allows the speed of the data transmission between the headset and the computing device 902 to be increased and more reliable.

The apparatuses and methods described herein may be used, in various embodiments, for fluid measurement (often fluid change measurement) in all parts of the body and for multiple medical diagnostic applications. The configuration of the emitter and detector (detector may alternatively be referred to by receiver) coils may be modified, in various embodiments, to be appropriate to the area of the body and/or the diagnostic application involved. For example, for an application involving a limb, such as the arm, or where it may be more important to measure liquid content at a shallow depth in the tissue, the emitter coil and detector coil may be placed on the same side of the subject tissue. A co-planar arrangement may be appropriate. Since the coils may be separated by a much shorter distance, the received signal strength may be much greater, and the size of the coils may be reduced. In various alternative embodiments, the coils may be in a side-by-side co-planar arrangement or in a concentric co-planar arrangement using coils with different diameters. In some embodiments, it may be more appropriate to place the plane of the coils at a slight angle to conform to the shape of the body part under study.

Figure 6:
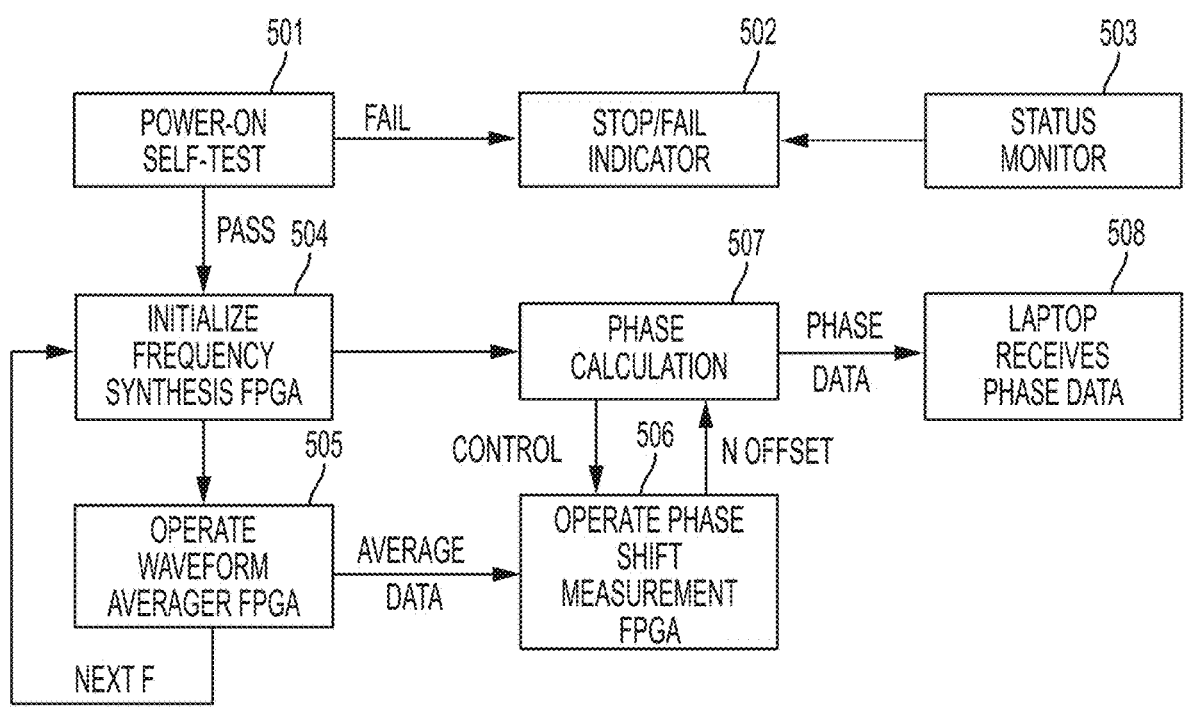
FIG. 6 is a flow diagram for the operation of the system of FIG. 1, according to one embodiment.

With the various examples of the systems described, a method of operating the system will now be described in more detail. With reference now to FIG. 6, one example of the operation of the system 100 will now be briefly described, it being understood that various operations illustrated in FIG. 6 will be described in more detail below, and various alternative methods and modes of operation will also be described below. Beginning at operation 501, the system 100 is powered on and a self-test is performed. If the system 100 fails the test, a stop or fail indicator is displayed on the laptop 102 in operation 502. If the system 100 passes the power-on self-test, operation moves to operation 504. Also, throughout operation of the system 100, a continuous status monitor may run in operation 503, and, should the status monitor determine that system 100 is failing, the system may display a stop or fail indicator in operation 502.

Once the system 100 passes the power-on self-test and operation has moved to operation 504, the frequency synthesis FPGA 110 may be initialized and begin to provide the transmitter 120 with the transmit signal in operation 504. The waveform averager FPGA 112 may begin to collect and average waveforms (e.g., fluid data) from the transmitter 120 and the receiver 124 in operation 505. The averaged waveforms may be provided to the phase shift measurement FPGA 114, which may determine the phase shift between the transmitter 120 and receiver 124 waveforms beginning in operation 506, with the ultimate phase calculation of interest being calculated in operation 507. The phase calculation may be provided to the laptop 102 in operation 508. At any point after operation 505, the frequency synthesizer FPGA 110 may provide another frequency to the transmitter 120, and the process may repeat for the next frequency. Multiple frequencies may thus be emitted from the transmitter 120 and subsequent phase shifts calculated. For example, the frequency synthesis FPGA 110 may provide the next frequency in repeated operation 504 while the phase shift measurement FPGA 114 measures the phase shift between the waveforms from the previous frequency, or the frequency synthesis FPGA may not provide the second frequency until the phase calculation has been provided to the laptop in operation 508. In an alternate embodiment, the emitter can emit a single frequency simultaneously with harmonic frequencies, or through the use of multiple frequency generators, for later separation using techniques such as Fast Fourier Transform (FFT). Simultaneous emission of multiple frequencies can be advantageous for noise cancellation, motion rejection and other purposes.

The Transmitter(s) and Receiver(s)

One range of electromagnetic frequencies appropriate for an inductive phase shift measurement based system 100 for brain fluid diagnostics is in the radio frequency (RF) range from about 20 MHz to 300 MHz, although other frequencies may also be used, such as between 1 MHz and 500 MHz, between 3 MHz and 300 MHz, and so forth. The frequencies chosen may provide relatively low absorption rates in human tissues, good signal relative to noise factors, such as capacitive coupling and signal line cross-talk, and ease of making accurate phase measurements.

Previously, certain examples of transmitters (and corresponding receivers) that emit (and sense) magnetic fields in these frequency ranges were constructed of thin inductive coils of a few circular turns placed such that the plane of the coil is parallel to the circumference of the head. The coils of these previous transmitters and receivers had diameters of 10 cm or more and 5 or more turns. These relatively large transmitter and receiver coils, however, were cumbersome and furthermore had resonances within the range of the frequencies of interest for VIPS detection of fluid in a human brain. When transmitter or receiver coils are operating in a frequency near one of their natural resonant frequencies, a measured phase shift may be largely a function of the magnitude of the coil's own parasitic capacitances, and very small changes due to motion of either of the coils and/or environmental effects can cause large changes in the phase shift, creating unacceptable noise in the measurement of phase shift.

Accordingly, in some embodiments of the present disclosure, the lowest natural resonant frequency of the transmitter 120 and/or receiver 124 may be higher than the intended frequencies of the magnetic fields to be transmitted. In some examples, the transmitter 120 may include a coil as a magnetic field generator or transducer. From symmetry considerations, this same or a similar coil may act as a magnetic field sensor in a receiver 124. In either case, as the diameter of the coil and number of turns (i.e., loops) is reduced the first self-resonant frequency generally increases. The limit, therefore, is for a coil with a single loop, the loop having a very small diameter. As the loop diameter decreases, however, the amount of magnetic flux intercepted by the loop is reduced by a factor equal to the ratio of diameters squared. Likewise, the induced voltage in the loop is reduced, resulting in a smaller signal from a loop acting as a magnetic field sensor in a receiver 124. Thus, there are practical limits on the diameter reduction. In some embodiments, however, an additional increase in the self-resonant frequency can be achieved by using transmission line techniques in the construction of the transmitter 120/receiver 124.

An alternative to using coils designed for a relatively constant phase shift over a wide bandwidth is to add external reactive components in a series-parallel network to tune out the phase shift at a single frequency or at a small number of discrete frequencies. This concept works best if the approximate value of the individual frequencies is known prior to designing the overall system and the number of discrete frequencies is small. By using switched or motor driven tunable components, the phase shift tuning can be automated and software controlled. An advantage of tuning to a constant phase shift is that it provides more freedom in the choice of the size and shape of the coils. Using larger coils can increase the detected signal strength and provide a field shape that is optimally matched to the portion of the brain or other body part that is being sampled.

Figure 2A:
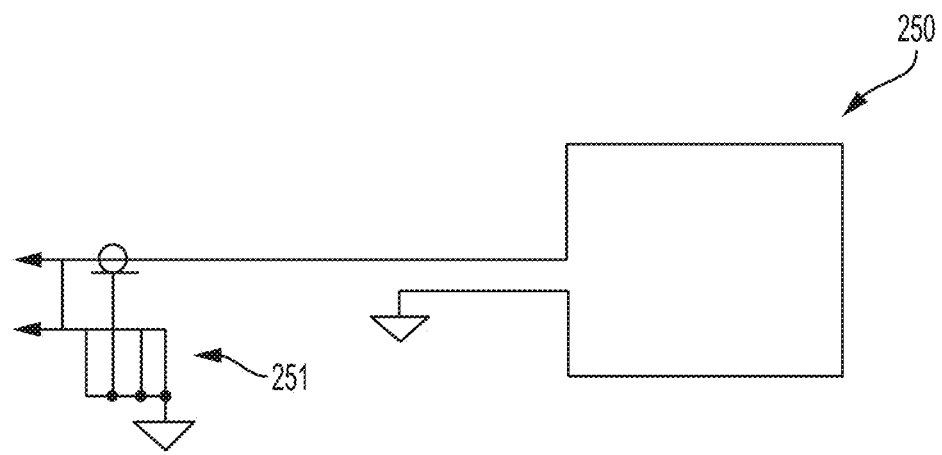
FIGS. 2A through 2F illustrate various embodiments of transmitter transducers and receiver sensors for use in the system of FIG. 1.

In one embodiment, with reference to FIG. 2A, a single loop 250 with a high self-resonant frequency and associated stable phase response below the self-resonant frequency may be constructed using a shielded transmission line, such as coaxial cable, buried strip-line on a printed circuit board, a twisted shielded pair of wires, a twinaxial cable, or a triaxial cable. The loop 250 may be used as either a magnetic field generator in the transmitter 120 or as a magnetic field sensor in the receiver 124. The shielded transmission line may include a first conductor as a shield 251 that at least partially encloses a second conductor. The first conductor or shield 251 may be grounded and may form a faraday cage around the second conductor. The second conductor may provide an output signal responsive to the changing magnetic field, and, due to the faraday cage, the second conductor may be shielded from external electrostatic effects and from capacitive coupling. For example, in one embodiment, a single loop 250 of buried strip line may be sandwiched between two grounded planes in a printed circuit board. A plurality of vias may extend between the two grounded planes, with the spacing of the vias determined by the wavelengths of the electromagnetic field being transmitted and/or received, and the vias together with the two grounded planes forming an effective electrostatic or faraday cage around the buried strip line loop 250. In other embodiments, other types of transmission lines with an outer shield (such as coaxial cable) may be used in order to form a faraday cage and thus reduce external electrostatic effects on the loop 250.

Figure 2B:
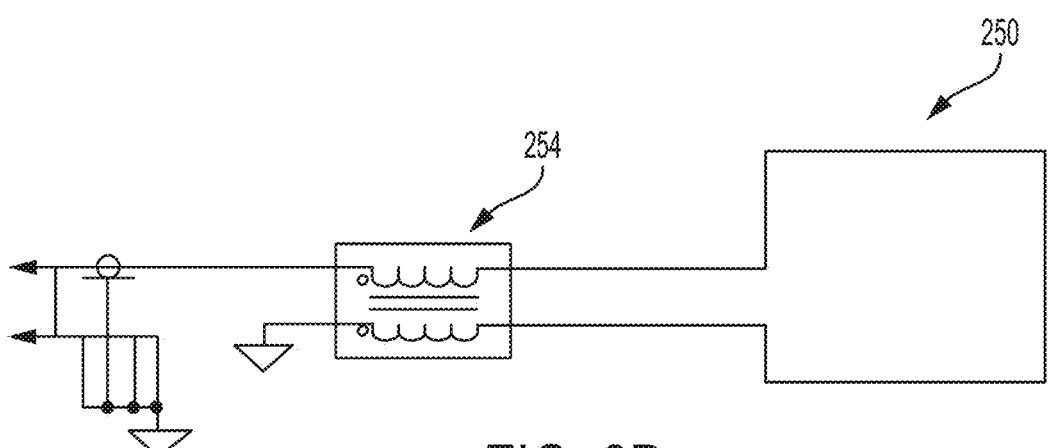
Figure 2C:
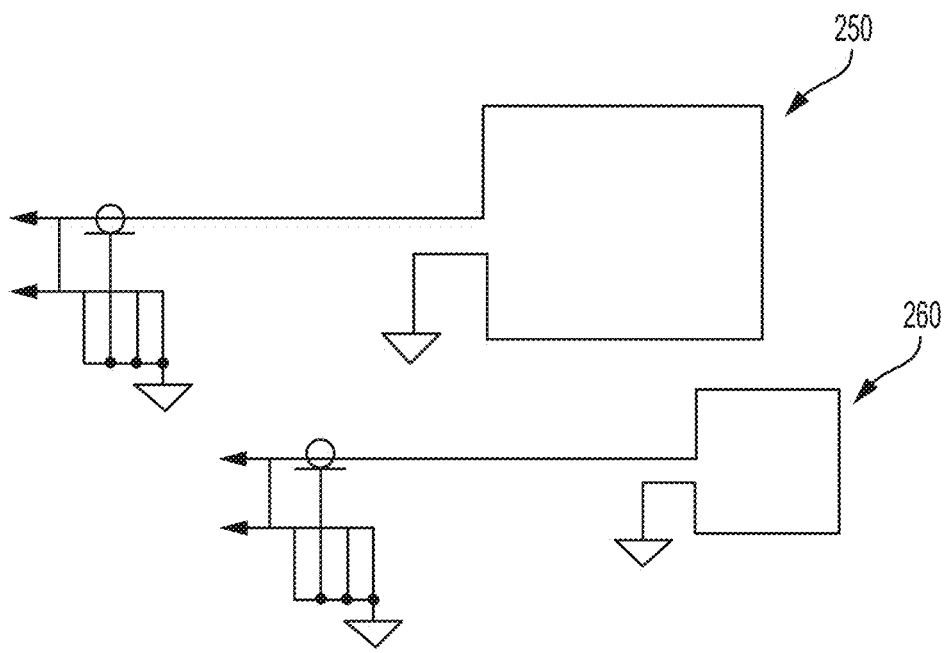
Figure 2D:
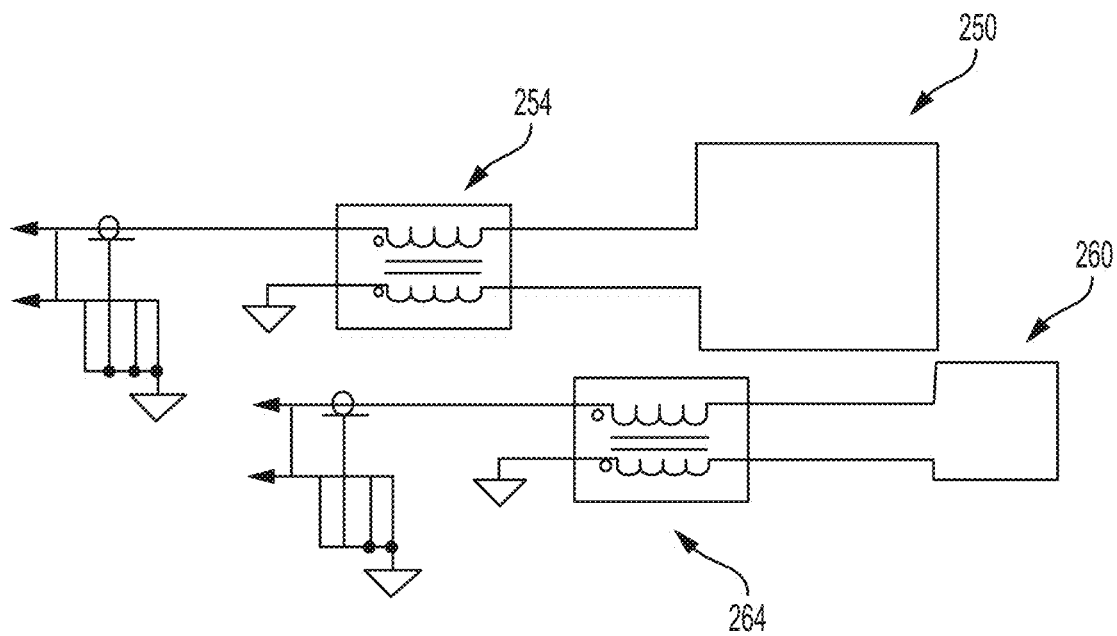

In single loop 250 embodiments of a transmitter 120 or receiver 124, the voltage of the loop 250 may not be in phase with the current of the loop 250 due to the inductive nature of the single loop 250. This phase error may be detected and accounted for during initialization of the diagnostic system 100, as described below. In some embodiments of the single transmitter loop 250, however, and with reference to FIG. 2B, a balun transformer 254 may be added, in order to obviate the need to correct for this phase error. In still other embodiments, and with reference to FIG. 2C, a second, independent, smaller, concentric loop 260 is used to sense the transmitted magnetic field and provide a current representative of the same to the A to D converter. The second, concentric transmitter loop 260 may in some examples be the same size as the corresponding receiver loop (e.g., in receiver 124) in order to have proportional signals and good uniformity between them, whereas in other examples the receiver loop may be larger than the second, concentric transmitter loop 260 in order to be more sensitive to the received magnetic field. In those transmitters 120 with the second, concentric transmitter loop 260, and with reference to FIG. 2D, a balun transformer 264 may likewise be used on this second, concentric loop 260 in order to balance the sensed voltage and current. Furthermore, for a single-turn receiver loop 250, a balun 254 may likewise be added in order to also balance its performance, similar to that shown for the transmitter cable in FIG. 2B.

Figure 2E:
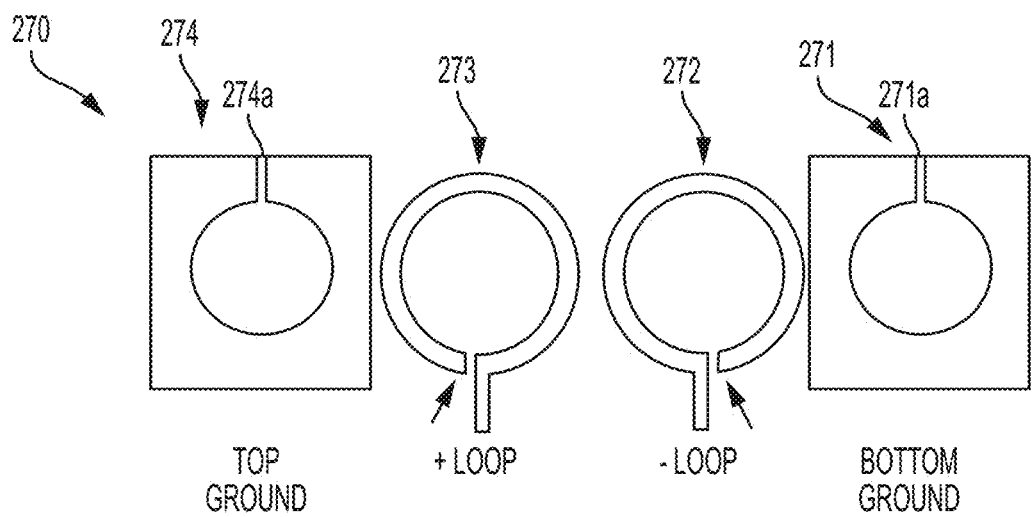

Referring now to FIG. 2E, in another embodiment, the transmission line concept may be extended from building a single-loop, single-ended device to building a dual-loop 270, which may be double-ended or "balanced," for use as a receiver 124 (or, symmetrically, for use as a balanced transmitter 120). In FIG. 2E, four conductive (e.g., copper) layers 271, 272, 273, 274 may be formed on a printed circuit board as shown, with three layers of dielectric material (not shown in FIG. 2E) coupled between the four conductive layers 271, 272, 273, 274 when stacked vertically. The top and bottom layers 271, 274 may be grounded and thus form an electric shield. Furthermore, small linear breaks 271A, 274a may be present in both of the top and bottom layers 271, 274 so that the ground planes 271, 274 don't act like additional shorted turns. In between the top and bottom ground layers 271, 274, the +loop 273 and the −loop 272 may be positioned, with the leads from the two loops 272, 273 being coupled to a balanced amplifier (not shown in FIG. 2E). The +loop 273 and the −loop 272 may be center tapped in some examples. The inner diameter of the two loops 272, 273 may be approximately 1 inch, and may be slightly greater than the inner diameter of the circular void in the two grounded planes 271, 274. In some embodiments, the thickness and permittivity of the dielectric material, the width and thickness of the conductive material forming the loops 272, 273, the spacing of the ground planes 271, 274, and so forth, may be chosen such that the double loop 270 has approximately a 50 ohm impedance in order to match the transmission line to which it will be coupled. In this manner, the self-resonant frequency of the dual loop structure 270 may be above 200 MHz in some examples.

Still with reference to FIG. 2E, for a dual loop 270 used as a magnetic field sensor in a receiver 124, external noise that is coupled into the system 100 from environmental changes in the magnetic field due to environmental EMI sources or motion of nearby conductors or magnetic materials may be reduced due to the common-mode rejection of the differential amplifier to which the two loops 272, 273 are coupled. Having the differential amplifier coupled to the loops 272, 273 when used as a receiver 124 thus may allow the loops' 272, 273 diameters to be reduced while keeping the output signal level at a suitable level for transmission to a remote processing unit 104 (e.g., for those systems where one or more A to D converters are not located directly in the headpiece 106). The amplifier power gain may be approximately 40 db in some embodiments. Low-cost wide-bandwidth amplifiers offering gains of 40 db for the power levels of interest are readily available in miniaturized packages from multiple suppliers with negligible phase shift variation over a 20 MHz to 200 MHz frequency range.

Figure 2F:
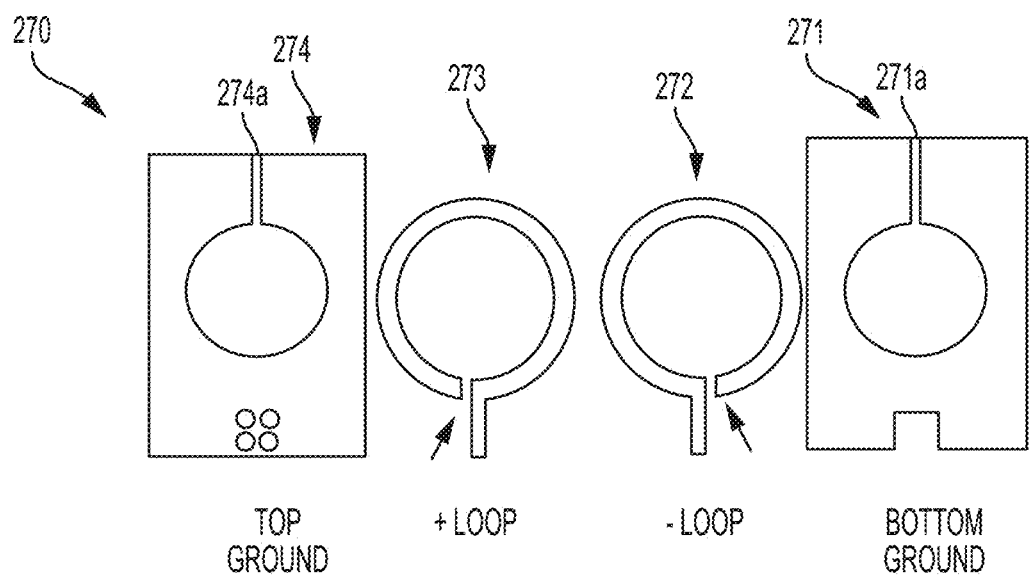

With reference to FIG. 2F, as suggested, the dual loop 270 used for a balanced receiver 124 has an analogous application as a magnetic field generating transmitter 120. The balanced approach for constructing a transmitter 120 may result in a common-mode cancellation of noise in the transmitted magnetic field due to the opposite winding directions of the dual loops, thus reducing noise in the transmitted magnetic field that may otherwise result from electrostatic or magnetic pickup from environmental factors.

Referring still to FIGS. 2E and 2F, in some embodiments, the two loops 272, 273 may be formed in different planes, or, in other embodiments, the two loops may be fabricated in the same plane with concentric circular strip-line traces (thus reducing the number of layers required in fabricating the pc board). This concentric design may be used for the transmitter 120, and/or the receiver 124.

Also, with reference to any of FIGS. 2A through 2F, in examples where the analog to digital conversion is not done proximate the transmitter 120 or receiver 124, a resistive attenuator may be added to the pc board with surface-mount resistors in order to help reduce cross-coupling of the transmitter signal to the receiver signal in the cable through which the analog signals are transmitted, which may help increase phase measurement accuracy and stability. The on-board attenuator may result in a substantial size and cost reduction compared with a bulky separate modular attenuator. Also, still continuing with examples where the analog to digital conversion is not done proximate the transmitter 120 or receiver 124, with reference still to any of FIGS. 2A through 2F, one or more amplifiers may be provided to amplify the signals from the transmitter 120 and/or the receiver 124 in order to reduce attenuation of the signals through the cable to the external analog to digital converter 122, 126. Still continuing with examples where the analog to digital conversion is not done proximate the transmitter 120 or receiver 124, the voltage on the transmitters and receivers may be in phase with current on the respective transmitters and receivers because the "balanced" transmitter and receivers illustrated in FIGS. 2E and 2F are terminated in the 50 ohm characteristic impedance of coaxial line.

Figure 3:
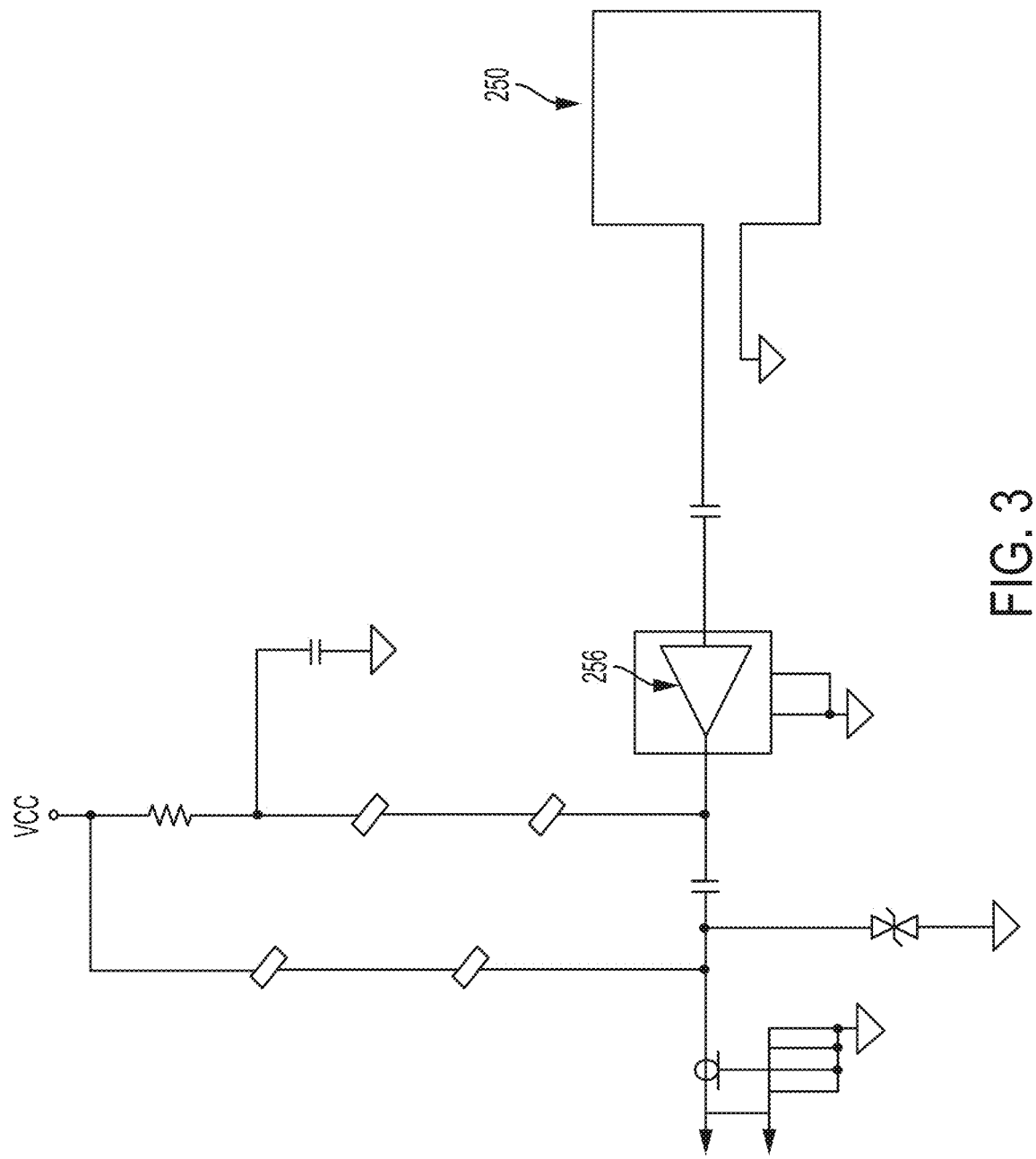
FIG. 3 is a circuit diagram of a phase shift detection apparatus, according to one embodiment.

Referring now to FIG. 3, an alternative design may include an amplifier 256 on the same printed circuit board as the loop 250. Including an amplifier 256 on the same printed circuit board as the loop 250 (that is used, for example, as a receiver 124) may help increase the signal to noise ratio, which may be particularly useful for embodiments where analog to digital conversion is done remotely from the headpiece 106. An amplifier 256 may also be used in embodiments where analog to digital conversion of a signal is done near the loop 250. As mentioned above, a balun transformer may be also included on the printed circuit board between loop 250 and the amplifier 256, which may help cause the coil to operate in a "balanced" mode. In the balanced mode, capacitively coupled electromagnetic interference pickup or motion induced fluctuations in the signal level may be reduced or canceled, since they typically equally couple into both the negative and positive leads of the balanced differential signal.

Initialization: Air-Scan to Remove Fixed-Phase Errors

As suggested above, the diagnostic system 100 may be initialized in some examples in order to calibrate the transmitter 120 individually, the receiver 124 individually, the transmitter 120 and the receiver 124 with one another and with the other associated electronics, and so forth. For example, variations in lead lengths and amplifier time delays in signal paths from the transmitter 120 and receiver 124 may be detected during initialization and removed from the signals during signal processing in order to prevent fixed offset errors in the data. Also, any phase shift between (measured) voltages and currents in a single-turn loop 250 may be detected.

The initialization may in one embodiment be an "air-scan" where the transmitter(s) 120 and receiver(s) 124 are positioned with only air between them, the transmitter(s) 120 and receiver(s) 124 positioned approximately as far apart as they would be if they were positioned on the head of an average patient. Once thus spaced, phase shift data is collected for a range of different frequencies (because the errors may be constant across or varying among different frequencies), and the collected air-scan values may be subsequently used during signal processing to correct any phase shift errors of the system 100 (e.g., by subtracting them from the values obtained during operation of the system 100). The initialization may be done when the A to D converters 122, 126 are in the headpiece 106 proximate to the transmitter 120 and receiver 124, when the A to D converters 122, 126 are external to the headpiece 106, and so forth.

Generation of the Driving and Sampling Signals

As mentioned above, the diagnostic system 100 collects phase shift data for transmitted time-varying magnetic fields at multiple frequencies because the phase shifts contributed by various tissue types and body fluids may vary with frequency. The diagnostic system 100 illustrated in FIG. 1 provides a flexible frequency synthesizer 100 within the processing unit 104, although in other embodiments, a frequency synthesizer 110 may be provided in, for example, the headpiece 106. This frequency synthesizer 110 may have a minimum of 1 MHz resolution over the range of about 20 MHz to 200 MHz in some examples (or alternatively about 20 MHz to 300 MHz or about 10 MHz to 300 MHz or any of a number of other suitable ranges). Standard digital phase-lock loop techniques may be used to derive the selectable frequencies from a single stable crystal-controlled clock oscillator. As described above, the digital portions of the synthesizer 110 may be implemented in one of the FPGAs 110 in the processing unit 104. The synthesizer 110 may produce both a basic square wave clock signal for generating the magnetic field in the transmitter 120 as well a sampling signal. The sampling signal may be at a slight offset (e.g. 10 KHz) in frequency from the magnetic field generating signal in some embodiments. The square wave signal for generating the magnetic field may, in some embodiments, be amplified to correct its level and may also be filtered to eliminate higher order harmonics and achieve a low distortion sine wave at one or more fundamental frequencies.

In other cases, where frequency domain techniques such as FFT processing of the time domain data are used to calculate phase, it may be advantageous to accentuate the harmonics of the fundamental frequency. For these embodiments, additional circuits may be added after the basic frequency synthesizer to make the rise-time or fall-time of a square-wave or pulse wave-shape much faster, thereby increasing the relative amplitude and number of higher order harmonics. As mentioned previously, this embodiment allows generation of a "comb" of frequencies with a single burst of RF and the processing of the captured time domain data from the emitter and detector using Fourier techniques yields a simultaneous time correlated phase difference data set for each frequency in the "comb". This simultaneous capture of phase data from multiple frequencies may yield significant advantages for separating the desired information about the patient's brain fluids from motion artifacts or other effects that would affect an individual scan of the frequency where the phase data for each frequency is measured at different times. Sampling each frequency at different times in this case introduces noise that may be difficult to detect or remove.

As the signal used to generate the magnetic field is typically periodic, it may not be necessary to use a sampling frequency that is many times greater than the frequency of that signal to capture the phase information from a single cycle of the waveform, and instead an under-sampling technique may be employed in some examples. Under-sampling is similar to heterodyning techniques used in modern radios where a large portion of amplifier gain and the audio or video signal demodulation is performed in much lower intermediate frequency stages of the electronics (IF). Under-sampling, in effect, allows a system to collect the same or a similar number of sample points over a longer period of time, while not disturbing the phase information of the signal.

Using under-sampling may eliminate the need for high-speed A to D converters (which are expensive and may involve many different wired connections) that may otherwise be required to capture enough phase samples from a single cycle of the waveform to accurately measure phase angle. If a lower speed A to D converter may be used, it may be commercially and physically practicable to position the A to D converter 122, 126 proximate the transmitter 120 and receiver 124 loops 250, 270, as described above.

Therefore, in some embodiments, one or both of the transmitted and received magnetic field signals may be under-sampled (e.g., with one sample or less for each cycle) and an average record of the waveform may thus be captured using samples taken over a much longer interval of time compared to one cycle. In order to accomplish the under-sampling, both the transmit signal and the sampling signal may be derived from a common clock signal, with the sampling signal being accurately offset from the transmit signal frequency (or a sub-harmonic frequency) by a small amount. If the offset is, for example, 10 KHz from the first harmonic frequency of the transmit signal, the result after a period of 100 microseconds will be an effective picture of one cycle of the repetitive transmit waveform with f/10000 individual samples. For a transmit signal frequency of 100 MHz and sample frequency 100.010 MHz, the 10,000 under-sampled individual samples of a single cycle of the transmit waveform are spaced at a resolution of 360/10000 or 0.036 degrees. As one alternative to under-sampling, frequency conversion using standard non-linear mixing technology before an A to D converter 122, 126 may also be employed.

In other examples, the frequency of the magnetic field generator signal and the frequency of the sampling signal may be otherwise related, one example of which is described below when referring to frequency domain signal processing techniques. In still other examples, the sampling frequency may be relatively constant (e.g., 210 MHz, while the generating frequency may vary over a wide range).

Conversion of the Transmitted and Received Analog Signals to Digital Data

In some embodiments, electronic phase shift measurements between the transmit and receive signals may be performed using analog signal processing techniques, whereas in other examples the phase shift measurements may be performed after converting the analog data to digital data through one or more A to D converters 122, 126, as described above. The digital waveforms may then be processed to obtain the relevant phase shift information. Processing digital data rather than analog data may facilitate sampling and averaging many cycles of the waveforms in order to, for example, reduce the effects of random noise and, with proper techniques, even reduce non-random periodic noise such as AC line pickup at frequencies near 60 Hz. Also, after reducing the noise in the waveform data there are many methods, such as correlation, that may be employed to obtain accurate phase measurement using digital signal processing.

In some examples of the diagnostic system 100 described herein, the A to D conversion of both the transmitted and the received signals is performed as close as feasible to the point of generation and/or detection of the magnetic fields. For example, the A to D conversion may performed in the headpiece 106 by miniaturized monolithic single chip A to D converters 122, 126 located integral to the printed circuits that, respectively, contain the transmitter 120 and receiver 124. The A to D converter 122 for the transmitter 120, for example, may differentially sample the voltage across the balanced outputs of the transmitter 120 in one example. The A to D converter 126 for the receiver 124, for example, may be positioned at the output of a wide bandwidth signal amplifier coupled to the receiver 124. By locating the A to D converters 122, 126 on the headpiece 106 rather than in a remote processing unit 104 (which may, however, be done in other embodiments described herein) it may be possible to reduce or eliminate the effects of phase shifts associated with motion, bending, or environmental changes on the cables carrying the analog signals to the A to D converters 122, 126. Other sources of error that may be reduced or eliminated include cable length related standing-wave resonances due to small impedance mismatches at the terminations and cross-coupling between the transmit and receive signals on the interconnecting cables that generate phase errors due to waveform distortion. To realize similar advantages in an embodiment where the A to D converters 122, 126 are not located proximate the transmitter 120 and receiver 124, a single cable may be used to bring the sampling signal to the transmitter and receiver A to D converters 122, 126 in the processing unit 104, and/or a high quality semi-rigid cable may be used between the two A to D converters 122, 126 in some embodiments.

Overall Operation and Pipelining

Referring again to FIG. 1, the waveform data (which may be under-sampled in some embodiments) may be captured for both the transmitted and received magnetic fields, and the captured waveforms may be at least partially processed in real-time (or substantially real-time). As described herein, one FPGA 112 may average the data for each of the two waveforms over many cycles for noise reduction. Another FPGA 114 may then use a correlation technique to perform a phase shift measurement using the averaged waveform data. A pipelining technique may be used in some embodiments to speed up the data throughput for collection of phase data over multiple frequency samples. The transmitter 120 may generate a time-varying magnetic field at a first desired frequency, and the requisite number of waveform averages may be performed by the waveform averager FPGA 112 at this first frequency.

After the averager FPGA 112 collects and averages all of the sample data points from the transmitter 120 and receiver 124, it may transfer the same to the phase shift measurement FPGA 114. In some embodiments, only a single transmit frequency is used in diagnosing a fluid change in a patient, but in other embodiments, a plurality of different transmit frequencies within a desired spectral range may be generated and the corresponding data collected. In those embodiments with multiple transmit frequencies, phase determination for a first transmit frequency may proceed in the phase shift measurement FPGA 114 (using the data acquired during the first transmit frequency) while the frequency synthesizer FPGA 110 causes the transmitter 120 to generate a magnetic field having a second desired frequency of the spectral scan and the waveform data from the second transmit frequency is averaged by the waveform averager FPGA 112 (hence the pipelining). In other embodiments, the waveform averaging for one transmit frequency may occur substantially simultaneously with recording a plurality of samples for a second frequency. In general, many different types of pipelining (e.g., performing two or more parts of the signal generation, acquisition, and data processing at substantially the same time) may be used. In other embodiments, however, there may not be any pipelining, and the diagnostic system 100 may transmit, collect, average, and process all of the data relating to a single transmit frequency before moving to a second transmit frequency.

Regardless of whether pipelining is used, the process of using different transmit frequencies may be repeated for any number of transmit frequencies with a desired spectral frequency scan, and may also be repeated for one or more frequencies within the spectral scan. The calculated phase shifts for each frequency may be transferred to the laptop 102 directly from the phase shift measurement FPGA 114 in some examples.

Signal Processing—Averaging

Because of the relatively small size of the transmitter 120 and the receiver 124, as well as the relatively low power of the transmitted magnetic field (it is low power because of, among other things, the need to protect a patient from overexposure to RF radiation and the need to minimize electromagnetic field emissions from the system 100), the measured magnetic field at the transmitter 120 and/or at the receiver 124 may have relatively large amounts of noise compared to its relatively small amplitude. The noise may include input thermal noise of an amplifier, background noise from EMI pickup, and so forth. In some embodiments, the noise may contribute a significant fraction to the phase shift measurements relative to the actual phase shift. For example, 1 ml of fluid change may correspond with a 0.3 degree phase shift, and thus if the noise in the transmit and receive signals is a substantial portion of, or even exceeds, the expected phase shift, the noise may render the data unacceptable.

In order to reduce the noise, the diagnostic system 100 described herein may, in some embodiments, sample many cycles of the transmitted and received magnetic fields (e.g., many multiples of 10,000 samples, such as 32,000 samples) and may average the individual samples in order to substantially reduce random noise or filter specific frequencies. In some examples, the total sampling time interval may be extended to be an approximate integer multiple of one 60 Hz AC power period in order to reduce the effect of 60 Hz related electromagnetic interference pickup. As explained below, these waveforms may be averaged by any appropriate averaging technique, including multiplying them by one another in the time domain, as well as other frequency domain averaging techniques.

Figure 4:
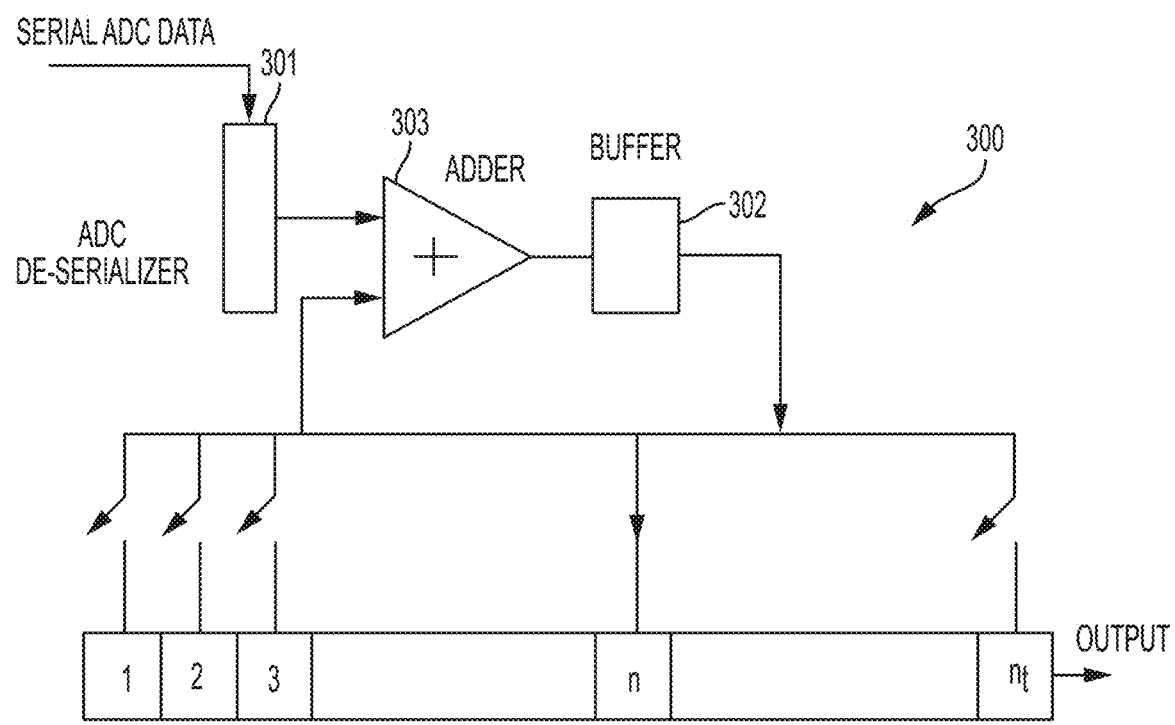
FIG. 4 is a simplified logic diagram for a waveform averager processor for use in the system of FIG. 1, according to one embodiment.

Referring now to FIG. 4, one embodiment 300 of a simplified logic diagram of the waveform averager FPGA 112 is shown. Of course, in other embodiments, custom circuitry may be employed to average data, which custom circuitry may be located in headpiece 106, in processing unit 104, in laptop 102, or in another suitable location. FIG. 4, however, illustrates one example of logic that may be implemented in the waveform averager FPGA 112 for averaging the transmitted waveform samples after they have been digitized by an A to D converter. Similar logic 300 may be used to average the received waveform samples after they have been digitized. The input to the waveform averager FPGA 112 may be a low voltage differential signaling (LVDS) type of format from the A to D converter, in order to reduce the wiring needed between an A to D converter and the waveform averager FPGA 112. In the LVDS format, each word of digital data representing a single waveform data-point may first be converted from serial data to parallel data by the deserialization logic described below.

The logic illustrated in FIG. 4 includes a synchronous serial-in, parallel-out shift register 301 that is clocked by the data transfer clock from the A to D converter. The parallel data words are then transferred into a memory buffer 302 with sufficient capacity to handle the maximum number of individual waveform samples required to construct one complete cycle of the transmitted waveform. An adder 303 may be used to accumulate the sum of all of the waveform samples in the memory buffer 302 as the data words exit the register 301 or after the memory buffer 302 is fully populated. Each waveform sum memory location may have a word size in bits that can accommodate the largest number expected for the sum without overflow. For example, a 12 bit resolution A to D converter and 4096 waveform sum requires a 24-bit memory word size. After accumulating the sum of the intended number of waveforms in the waveform memory for the transmitted signal samples (and, separately, the receiver signal samples are similarly summed in a waveform averager), the memory contents for both waveforms are serially transferred to the phase shift measurement FPGA 114. It may not be necessary to divide by the number of waveforms being averaged in some examples because, in the next step of the processing, only the relative magnitudes of the data-points in the averaged waveforms may be relevant. Because of this, an appropriate number of least significant bits may also be deleted from each of the averaged waveform data points without significant impact to the accuracy of the overall phase shift determination.

Signal Processing—Determining Phase Shift

Figure 5:
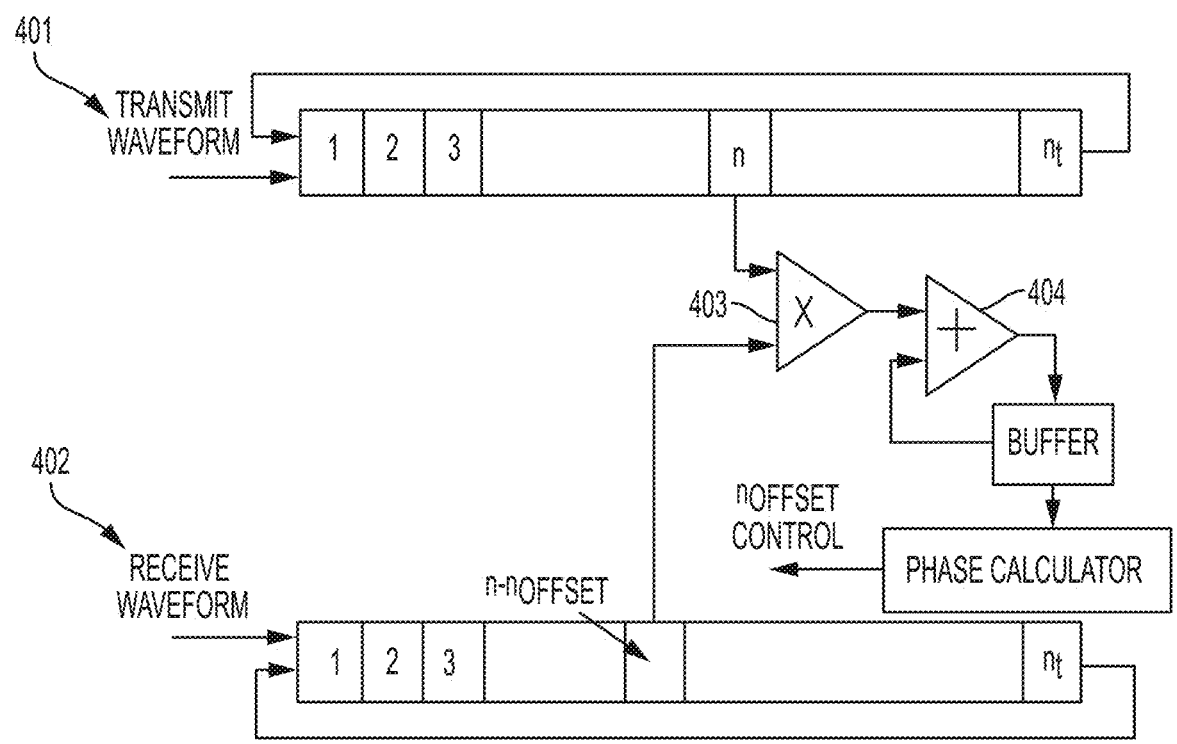
FIG. 5 is a simplified logic diagram of a phase shift measurement processor for use in the system of FIG. 1, according to one embodiment.

Referring now to FIG. 5, the phase shift measurement FPGA 114 may also contain two revolving shift registers 401, 402, a multiplier 403, and an adder 404. It may also include logic configured to calculate the sum of the product of the individual transmit and receive averaged waveform data points with an adjustable phase shift between the two waveforms. The FPGA may be used to find the phase shift where the sum of products is closest to zero and the slope of the sum of products versus phase shift is also negative.

Consider the following trigonometric identity for the product of two sine waves with frequency f and phase shift $\Phi$:

$$\sin u \sin v = \frac{1}{2}[\cos(u-v) - \cos(u+v)] \quad \text{(Eq. 1)}$$

where $u = 2\pi ft + \Phi$ and $v = 2\pi ft$ $$= \frac{1}{2}[\cos(\Phi) - \cos(2\pi(2F)t + (\Phi))] \quad \text{(Eq. 2)}$$

The first term of the product is a DC term dependent only on the phase shift. The second term is another sine wave at twice the frequency which averages to zero over one complete cycle of the original frequency. Note that the first term (a cosine wave) is also zero when the phase angle ($\Phi$) is either +90° or −90°. Furthermore the slope of the product with respect to phase angle changed (sin u sin v)/d$\Phi$) is negative for $\Phi$=+90° and positive at $\Phi$=−90°.

By iteration, the FPGA may determine the value of $n_{offset}$ where the transmitted wave and received wave are closest to a +90° phase shift. For an offset of $n_{offset}$ samples, and $n_t$ samples for one complete 360° waveform, the phase shift is then calculated using the following equation:

Phase shift=90°+($n_{offset}/n_t$)*360°  (eq. 3)

The resolution of the determination may be limited to the number of samples (resolution=360°/$n_t$). If this resolution is insufficient for the needed precision of the measurement, then interpolation may be used to find the fractional value of $n_{offset}$ where the sum of product terms exactly passes through zero.

Frequency Domain Signal Processing Methods for Phase Shift Measurement

As explained above (see e.g., sections on averaging and multiplying waveforms together to obtain phase shift data), the signal processing of the measured and digitized magnetic field traces from both the transmitter 120 and the receiver 124 may proceed in the time domain. In other embodiments, however, the signals may be processed in the frequency domain using, for example, Fast Fourier Transforms (FFTs)

In one embodiment of Fourier domain analysis, the signals from the transmitter 120 and receiver 124 are digitized at, for example, about a 200 MHz sampling rate with a relatively high resolution (e.g., 14 bits). The A to D converter and the data capture electronics may be included in a relatively small printed circuit assembly packaging. The captured data may be transferred via a high-speed USB serial link to the laptop computer 102. Time domain processing can then be replaced by frequency-domain processing on the laptop 102 to calculate the phase shift between the waveforms.

Once the data is on the laptop 102, the FFT for each of the transmitter and receiver time domain waveforms can be calculated (in other embodiments, however, the FFT may be calculated by an FPGA or other processor proximate the A to D converters). The resulting real and imaginary solutions which represent the resistive and reactive frequency domain data can then be converted from cartesian to polar coordinates, thus yielding frequency domain plots of the magnitude and phase of the waveforms. The phase of each waveform can be obtained from the frequency domain plots of phase for the frequency of interest. If the fundamental frequency is off-scale, then a difference frequency between the sampling frequency and the transmitted wavefield frequency can be used. For example, a sample frequency of 210 MHz yields an FFT with a frequency range of 0 to 105 MHz, and the fundamental frequency is used for phase shift measurement when the transmitted wavefield frequency lies in this range. The difference frequency is used if the transmitted wavefield frequency is in the higher end of the range, for example, 105 MHz to 315 MHz.

After the FFT for both of the transmitted and received wavefield signals is calculated, the phase shift for a particular frequency of interest can then be calculated from the difference of the phase values obtained from the transformed transmitter and receiver waveforms. Note that some sign reversals for the phase information in various frequency regions may be needed when calculating the shift.

In order to allow FFTs to be computed for samples from the transmitter 120 and the receiver 124, the frequencies used for the sampling and the transmitted waveform may be determined so as to allow coherent sampling so that both the transmitted and received waveforms contain an integer number of complete time periods of the repeated waveform, and the number of samples collected for the waveforms is an even power of two. One method for implementing coherent sampling is to choose transmitter and receiver sampling frequencies such that $prime_1/f_{transmit}$=$prime_2/f_{receive}$. The prime numbers $prime_1$ and $prime_2$, as well as the number of samples, can be very large in some embodiments, thereby reducing the spacing between the allowable values for the signal frequencies (e.g., the tuning resolution may be approximately 1 Hz). This may be accomplished by using digital frequency synthesis techniques, such as by combining a stable frequency source and the appropriate combinations of integer frequency multipliers, integer frequency dividers, and phase lock loops.

With coherent sampling, the theoretical accuracy of the phase calculation may only be limited by the number of samples of the time domain waveform and the digital resolution of the A to D converter. Dc noise and low frequency noise sources such as 1/f noise may be inherently rejected by the frequency domain processing technique. The use of coherent sampling also reduces the probability that harmonic and intermodulation product frequency components will lie on top of the frequencies of interest for calculating phase. Furthermore, using an FFT frequency domain solution to determining phase may provide information regarding the magnitude or amplitude of the measured transmitted and received magnetic fields. The ratio of the magnitude values can be used to determine the attenuation of the transmitted magnetic field, which may be expressed in logarithmic dB power ratio units.

Alternative Signal Processing in the Time Domain

As one additional alternative signal processing technique in the time domain, the phase shift measurement may be done via one or more relatively low-cost analog phase detectors or by measuring time delays between zero crossings of the transmitted and received wavefield signals. For example, an integrated phase detector circuit may include an amplifier that converts sine waves of transmitted and received wavefields to square waves by clipping the sine waves (e.g., with an extra high gain), and then compares the clipped/square wave from the transmitter with that from the receiver using an analog exclusive OR (XOR) gate, with the pulse width provided by the XOR gate being indicative of the phase shift between the transmitted and received magnetic fields.

Reduction of Phase Measurement Errors Due to Motion

Among all of the factors that contribute to phase measurement error, many are related to motion—motion of the patient, movement of the transmitter 120, movement of the receiver 124, bending of the connection or transmission cables, etc. For example, relative motion between the patient and the transmitter 120/receiver 124 results in path length and location variations for the magnetic field lines as they pass through the patient's head. Conductive or magnetic objects moving near the transmitter 120 and/or near the receiver 124 can also change the shape of the magnetic field lines as they pass from the transmitter 120 to the receiver 124.

In some embodiments, methods may be deployed to reduce artifacts attributable to patient movement. These algorithms may, for example, detect statistical variations in the differential phase shift data across the frequency spectrum of interest (e.g., from about 30 MHz to 300 MHz or about 20 MHz to 200 MHz) that could not possibly be the result of biological changes, as determined by their rates of change or other characteristics. This thresholding-type of method may thus be used to eliminate data corrupted by means other than true biological changes.

As another example, the attenuation data that is obtained from the magnitude portion of the FFT processing can be used in algorithms by examining the way it varies across the frequency spectrum to aid in the detection and correction of motion artifacts in the phase shift data.

As still another example, electronic accelerometers can additionally or alternatively be used to detect motion of one or more of the transmitter 120, the receiver 124, the patient, or the transmission cables. In some examples, accelerometers may be coupled to the same printed circuit board as the transmitter or receiver (e.g., using a MEMS type accelerometer).

In addition to detecting any motion above a threshold level, a relationship between the transmitter/receiver accelerometer data and patient accelerometer data may be examined for relative differences. For example, small amplitude changes sensed in both the patient and the transmitter/receiver may be of little consequence. Some patient motion is almost always present (because, e.g., even comatose patients breathe). Larger or non-correlated accelerometer readings, however, may be used to trigger data rejection or correction. Because the separate motion of totally independent objects near the patient can also present motion artifacts in the data then some types of motion detection and correction based on statistical analyses of the phase data may still be required.

Medical Diagnostic Methods for Alerting Clinicians

The system 100 described herein may be used to, among other things, measure the change in phase shift induced by changes in fluid content within, for example, a patient's head ("intracranial fluid"). Methods can be employed to analyze the phase data and make a determination as to whether the fluid change represents a tissue change that is troubling to the clinician user. For example, a baseline reading of the phase shift between a magnetic field transmitted from a transmitter 120 positioned on one side of a patient's head and a magnetic field received at a receiver 124 positioned on the other side of the patient's head at one or more frequencies may be recorded when the patient first arrives at the hospital. Then, any significant changes in the measured phase shift that occurs during subsequent scans can be tracked and trended by clinicians to aid in understanding the patient's clinical condition, and certain thresholds, patterns or trends may trigger an alarm. Many methods may be employed and optimized to provide the clinicians with the most useful fluid change information. For example, if the phase shifts by more than a certain number of degrees, the system may sound an alarm to alert the clinician that the patient may have clinically significant bleeding or edema. For some conditions, it may be useful to alert the clinician if the rate of change of the phase shift exceeds a threshold.

The phase shifts at different frequencies may vary with different fluid changes, as described, for example, U.S. Pat. No. 7,638,341, which is hereby incorporated by reference in its entirety for all purposes. Certain patterns of phase shift may be correlated with certain clinical conditions. For example, a condition such as bleeding or edema may be evidenced by an increase in phase angle at one frequency, with a concurrent decrease at a different frequency. Using ratios of phase shifts at different frequencies can provide additional information about the types of fluids and how they are changing. For example, the ratio of phase shift at a first frequency to the phase shift at a second frequency may be a good parameter to assess blood content or to separate edema from bleeding or other fluid change. For example, the phase shift frequency response of saline may be different from the phase shift frequency response of blood, thus allowing a clinician to separately identify changes in blood and saline content in a patient's brain cavity. Changes in amounts of water may have relatively little effect on phase shift in some instances, although the concentration of electrolytes in an ionic solution may have a more pronounced effect.

The phase shift patterns may also be time dependent. A hypothetical clinical condition may be characterized by an increase in phase shift for some period of time, then stabilizing, and then returning to baseline after some other time period. Noise factors such as patient activities like getting up out of bed, eating, getting blood drawn or speaking with visitors may cause changes to the phase shift readings from baseline. Clinically meaningful fluid changes may be differentiated from noise by examining the patterns associated with different activities.

Using combinations of phase shift and/or attenuation data at various frequencies, ratios or other functions of those phase shifts and/or attenuations, and/or time-based methods may all be combined and optimized in various embodiments to provide a range of useful information about tissue and/or fluid changes to clinicians. The clinicians can then respond to the tissue changes by using more specific diagnostic techniques such as medical imaging to diagnose a clinical problem.

In some cases, therapies may be changed in response to fluid and/or tissue change information. For example, the diagnostic system described herein may monitor fluid changes in a patient who is on blood thinners to dissolve a clot in a cerebral artery. If the system detects an intracerebral bleed, the blood thinners may be reduced or stopped to help manage the bleeding, or other interventions such as vascular surgery may be performed to stop the bleeding. As another example, a patient who begins to experience cerebral edema may undergo medical interventions to control or reduce the edema, or can undergo surgical procedures to drain fluid or even have a hemicraniectomy to reduce intracerebral pressure due to the edema.

Clinicians may, in some cases, use fluid change information to manage medication dosage by examining what is effectively feedback from the diagnostic system. For example, if mannitol is used to reduce intracerebral pressure by drawing water out of the brain, a treating clinician may use the diagnostic system described herein in order to receive feedback regarding how the patient's brain water is changing in response to the medication.

Similarly, drugs for blood pressure management, electrolyte concentration and other parameters may be more effectively administered when dosage amounts are controlled responsive to feedback from the diagnostic system described herein. For example, cerebral sodium concentrations may be controlled using intravenous hypertonic or hypotonic saline solutions. Changes to the ion concentrations can be detected as a shift in phase angle or some function of shift in phase angle at one or more frequencies. Such information can be used as feedback to the physician to better manage the patient.

Additional Embodiments

One embodiment of a VIPS system for monitoring intracranial/brain fluid(s) houses all of the electronics in the headpiece 129. The headpiece 129 could be constructed like a helmet or hardhat. The radiofrequency oscillators can be placed near the emitter or multiple emitters 120/124, potentially on the same printed circuit board. One oscillator can generate the transmitter signal, and another oscillator can be used to generate the sampling signal. As will be discussed later, multiple transmitters or receivers may be used, and it may be desirable to have different oscillators for different transmitters. Therefore, multiple oscillators may be used. In another embodiment, the headpiece 129 could be constructed like a pair of spectacles. One advantage of such an embodiment is that the position may be better controlled because the device would be mechanically registered to the nose and two ears, making it possible to remove and replace the device with good repeatability of antenna location. The antennas can be placed on the temples of the glasses, just above and in front of the ears, providing a location approximately at the center of the brain. The antenna placement near the ears has the feature of being close to the mechanical reference points, and therefore providing for good position repeatability.

In some embodiments, multiple transmitters may be used, transmitting frequencies that are offset from each other. For example, three transmitter antennae may be used, and each antenna may transmit a frequency that is several KHz different from the others. The frequency of all three oscillators should be derived from the same stable reference oscillator, using digital phase locked loop synthesis techniques to reduce phase errors due to the differences in thermal frequency drift and phase noise of separate oscillators. One advantage of having slightly different frequencies for each transmitter is that the system could then identify and separate out the signals produced from each transmitter, for example, using a Fast Fourier Transform (FFT). Using this technique, all transmitters could briefly be powered on simultaneously, and all of the received phase information for each transmitter/receiver combination could simultaneously be determined using FFTs of the transmitted and received waveforms for the same extremely small time interval. This information can allow the system to resolve the location of a fluid change within the tissue and also differentiate from phase changes caused by motion of the patient, tissue fluid flow, or motion of the antennae or field motion generated from moving objects in the environment. For example, such a system may be used to specifically identify the location of a hematoma or volume of ischemia inside the brain of a patient.

For medical applications, it may be desirable to transmit signals within the industrial, scientific and medical radio band (referred to herein as the "ism band"). However, it may be desirable to design the system to transmit outside this band so as to reduce exposure to more ambient radiofrequency noise coming from other devices operating in the ism band.

In order to improve the system's robustness against ambient radiofrequency noise, the system can detect the ambient radiofrequency noise during time periods when the oscillators are not transmitting any signals. If the noise at certain frequencies is too high, then the system can shift to generating signals at a different frequency, thus improving the signal-to-noise ratio. In some applications, it may be desirable to use spread spectrum techniques for measuring the phase, in order to spread the electromagnetic interference frequencies over a wider range of frequencies to improve the signal-to-noise ratio. To facilitate changing frequencies, multiple crystals could be installed in the device, and the system could select between the crystals to allow for selecting the most appropriate frequency given the noise environment. Alternately, the digital RF frequency synthesizer could have sufficient bandwidth and resolution to facilitate rapid frequency synthesis for the new frequencies from a single reference crystal oscillator. If necessary, the reference crystal oscillators could be oven stabilized to further reduce phase errors from temperate drift.

When generating the signals, a variety of wave shapes may be employed. A square wave will provide more power at harmonics of the fundamental frequency. Sine waves and distorted square waves can be used to push more of the radiofrequency power into the higher frequencies, or to provide power at various harmonic frequencies. Alternatively, a base frequency and higher frequency can be summed together for additional power at the different frequencies. A separate RF frequency may also be required for the sample signal for analog to digital conversion. For adequate resolution in the phase measurement, the required resolution on the sampling frequency may also be very high to allow coherent sampling. Digital frequency synthesizers could use various combinations of phase lock loop stabilized frequency multipliers and frequency dividers to achieve the high resolution needed for coherent sampling, while also generating the slightly offset frequencies for multiple transmitters. A receiver amplifier with high gain and good phase stability is needed. In one embodiment, amplification of about 40 dB of gain is used. In some embodiments, the receiver amplifier may employ two or more gain stages, for example, 20 dB on the antenna and an additional 20 dB on the analog-to-digital conversion board.

Analog-to-digital converters can also be included on the same printed circuit boards with the emitter and receiver antennas, along with any amplifiers that are appropriate to amplify the signals to an optimum level.

Data can be transferred from the helmet to the console with various high-speed cable connections and protocols. Using metal cables can induce a source of error by changing the shape of the magnetic field. To avoid this problem, fiber-optic cables can be used as an alternative to metal cables.

Data can be transmitted wirelessly from the patient headset or helmet to a console with a wireless protocol such as Bluetooth, WiFi, wireless, or other suitable protocol. The data transmitted can be time domain data, or an FFT can be performed by a processor in the headpiece, and the resulting digital data may then be sent wirelessly to the console. The primary advantage to sending the data in the frequency domain with an FFT is a reduction in the amount of data, resulting in a lower required data transmission rate. The FFT may be performed by a processing element, such as a field-programmable gate array (FPGA) hardwired to perform FFT inside the helmet. Alternatively, other types of microprocessors, including general-purpose microprocessors, could be used to perform the FFT. Because all of these electronics are mounted inside the helmet or other headpiece 129, in some embodiments, it may be advantageous to minimize the size and power consumption of the components. To further reduce the need for an electrical cable connection to the console, a portable rechargeable battery based power system may be included in the helmet.

In one embodiment, the system is designed to take multiple samples per second, either continuously or in short bursts, so that the data may be analyzed to measure a patient's heart rate, or provide other useful information. This technique may help to differentiate arterial from venous blood volume measurements, much like the technique used in pulse oximetry. In another embodiment, the system may be configured to synchronize to an EKG, pulse oximetry, or other cardiac signal. This may provide a very accurate timing trigger for measuring the arterial and venous blood volume simultaneously with a particular portion of the cardiac cycle. Synchronizing VIPS readings to an external cardiac signal allows under-sampling relative to cardiac rhythm, with VIPS readings which can be spaced seconds apart. By comparing VIPS readings at different portions of the cardiac cycle, a series of VIPS readings can be processed to reconstruct fluid composition changes associated with the cardiac rhythm, revealing a measure of the global perfusion within the brain.

Figure 7:
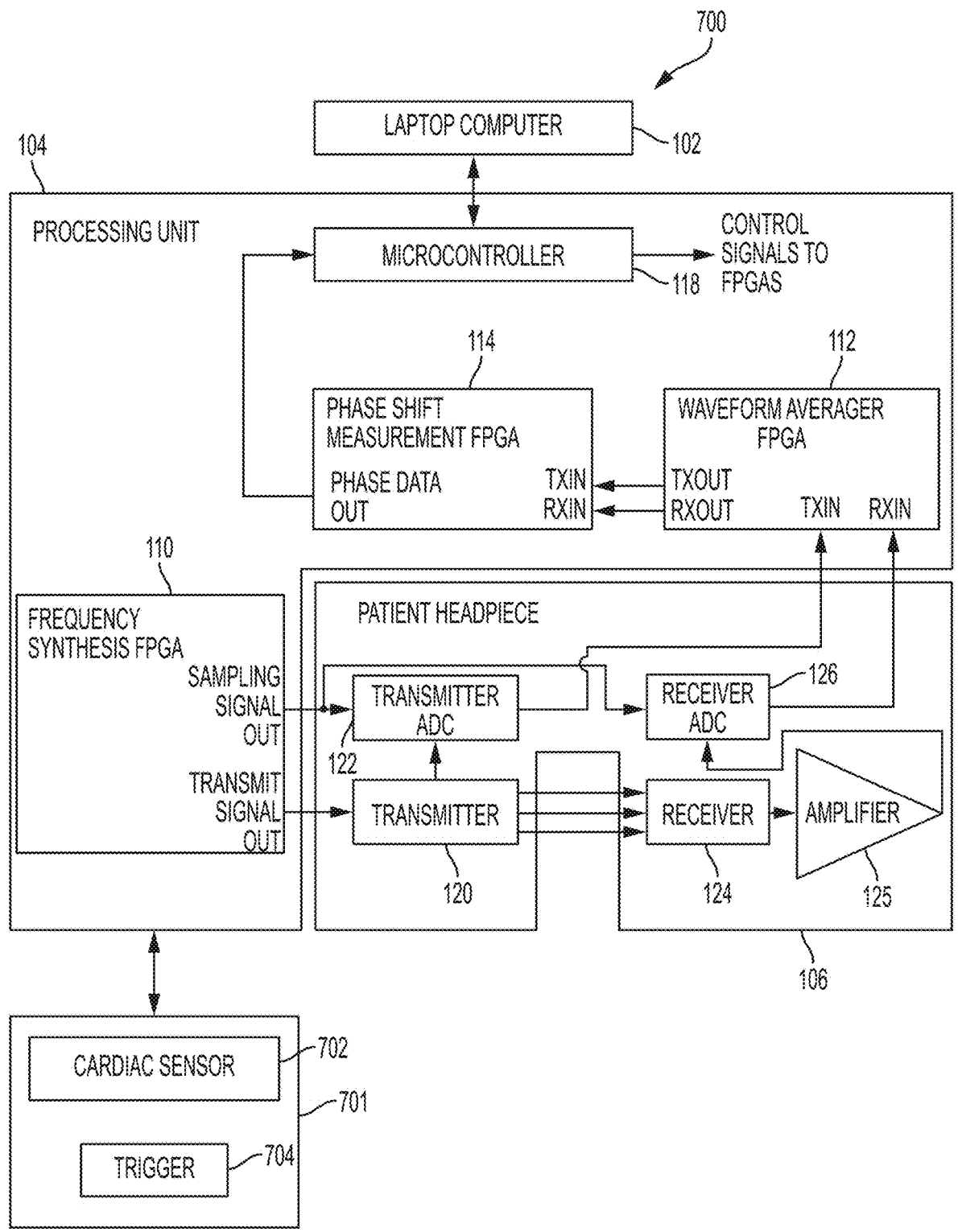
FIG. 7 is a block diagram of a system for monitoring fluid changes in a body corresponding to a cardiac signal, according to one embodiment.

An illustrative system for synchronizing VIPS readings with the cardiac signal will now be discussed. As should be understood, the embodiment of FIG. 7 may be modified with substantially any type of physiologic sensor for detecting variations in a patient's body and should not be limited to the cardiac signal specifically discussed. FIG. 7 is a block diagram of a system 700 for detecting and monitoring bodily fluid volumes due to or occurring with a cardiac cycle of the patient. The system 700 of FIG. 7 may be substantially similar to the system 100 of FIG. 1. However, in the embodiment of FIG. 7, the system 700 includes a cardiac module 701, which may include a cardiac cycle sensor 702 and a trigger 704. The cardiac cycle sensor 702 may be substantially any type of sensor or combination of sensors that detect the electrical activity of a patient's heart. For example, the cardiac cycle sensor 702 may be configured to detect the polarization and depolarization of cardiac tissue. The cardiac cycle sensor 702 may further be in communication with the processing unit 104, microcontroller 118, or other processing element that may transform the various signals into a cardiac waveform or other desired form. In a specific example, the cardiac sensor 702 may be a pressure sensor that detects changes in pressure within a patient's body to detect characteristics of the cardiac cycle. In another example, the cardiac sensor 702 may be an acoustic sensor that senses changes in sound to detect characteristics of the cardiac system. The cardiac cycle sensor 702 may be formed integrally with the headpiece 106 or may be a separate component therefrom.

The trigger 704 may be substantially any type of device that may receive and/or transmit signals. The trigger 704 may be in electrical communication with the cardiac sensor(s) 702 and may be configured to transmit a signal, such as an infrared pulse (open air or optical fiber), a radio frequency pulse, and/or radio frequency digital communication based timing pulse, to the processing unit 104 and/or headset 106.

Using the system 700 of FIG. 7, a VIPS measurement may be triggered wirelessly or wired by the trigger 704. For example, based on detection of a particular cardiac event (e.g., pulse oximetry) or other cardiac signal, the trigger 704 may indicate to the processing unit 104 to activate a VIPS reading, so that data may be detected and collected at specific portions of the cardiac cycle. In this example, the VIPS detection may be based on a cardiac event. However, in other embodiments, the detection antenna or wiring on the cardiac sensor 702 may be sensitive to VIPS radio transmission frequencies and may be configured to be activated by the VIPS in order to capture the instant of each VIPS data acquisition pulse within the EKG record (an augmentation and/or alternative means of assuring very accurate correlation of VIPS data to cardiac cycle data)

With each heartbeat, the volume of arterial blood, venous blood, and cerebrospinal fluid in the brain fluctuate, and these changes, as detected by VIPS monitoring, may yield valuable diagnostic information. In one embodiment, the system is designed to take multiple samples per second, either continuously or in short bursts, so that the data may be analyzed to measure a patient's heart rate. In another embodiment, the system may be configured to be triggered by and synchronized to an EKG, pulse oximetry, or other cardiac signal. This may provide a very accurate timing trigger for measuring fluid conditions, including arterial blood volume, venous blood volume, and cerebrospinal fluid volume at one or more particular portions of the cardiac cycle. This technique may help to differentiate arterial from venous blood volume measurements, much like the technique used in pulse oximetry.

In yet another embodiment, the VIPS measurements are not triggered to synchronize to an EKG or other external cardiac signal, but are time tagged with sufficient precision to assign each VIPS measurement to the portion of the cardiac cycle under which it was collected. By comparing VIPS readings at different portions of the cardiac cycle, either by synchronous acquisition or by subsequent analysis, a series of VIPS readings can be processed to reconstruct fluid composition changes associated with the cardiac cycle. Such analysis of VIPS measurements may reveal a measure of the global perfusion within the brain, as well as valuable information for the diagnosis of conditions, such as shunt failure (detailed later in the specification). These methods (synchronizing VIPS readings to an external cardiac signal or time-based correlation with an external cardiac signal) allow under-sampling relative to cardiac rhythm, so that individual VIPS readings may be spaced even many seconds apart, while still providing valuable information relating to fluid fluctuations associated with the cardiac cycle. Other examples include synchronizing (or isolating irregularities) to a ventilation signal, such as a capnography signal.

A variety of signal processing analysis techniques, including frequency domain approaches, such as discrete Fourier transforms (DFT) and Fast Fourier Transforms (FFT) analysis, may be applied to the VIPS measurements to reveal the frequency distribution of the oscillations in cerebral fluids, which derive from the patient's heart rate. These techniques may be applied to the measured VIPS phases and/or magnitude data for multiple radio frequencies, either alone or in combination. Useful combinations for analysis include theoretically and empirically derived formulae that use weighted combinations of VIPS phases and amplitude data to create indicators that correlate with blood volume, cerebrospinal fluids, edema, or other relevant fluid characteristics. When an external cardiac signal is available for correlation, the period and frequency of the cardiac cycle is provided and may be used with processing approaches, such as applying averages, medians, or other statistics to VIPS measurements at each of the measured portions of the cardiac cycle, then calculating the differences between bins to determine the magnitudes of the fluid changes associated with the cardiac cycle.

In another embodiment, the system is designed to take multiple samples per second and is configured to generate a signal that corresponds to the magnitude of the change in intracranial blood volume that results from each arterial pulse. It is well known in the art of intracranial pressure (ICP) measurement that ICP increases during the diastole phase of the cardiac cycle, and decreases during systole, because of the induced changes in intracranial blood volume. Using an ICP monitor, therefore, a plethysmogram can be generated, which approximately plots the intracranial blood volume over time as it fluctuates through repeated cardiac cycles.

The amplitude of ICP changes due to cardiac pulsation is significantly damped in patients who have cranial vents, for example, an intraventricular catheter. This is because the pressure pulses are relieved as fluid moves back and forth through the catheter. The same dampening of the ICP plethysmogram occurs in patients with intraventricular shunts, as are commonly used in patients with chronic hydrocephalus. When the shunt is working normally, cerebrospinal fluid will move back and forth in the shunt catheter, dampening the ICP excursions during cardiac cycles. However, when the shunt is clogged or otherwise malfunctions, the fluid is unable to move during cardiac cycles, and the amplitude of the ICP variation increases. The current invention can be configured to monitor the changes in blood and cerebrospinal fluid volumes that result during cardiac cycles and detect shunt clogs or malfunctions.

Once a plethysmogram is generated, there are a variety of ways one can use the information to help to diagnose the condition of a patient. For example, after the peak of the cardiac pressure/volume pulse, the following portion of the waveform represents the recovery period during which the fluid volume returns to baseline. The time it takes from the peak to another subsequent point in the cardiac cycle can provide information about intracranial compliance or intracranial pressure. It can help identify specific characteristics of intraventricular shunt performance or failure. Ratios, differences and other mathematical relationships of amplitudes of the plethysmogram at various time points along the cardiac cycle can be developed to indicate a variety of clinical conditions and physiologic parameters.

There is a need during administration of cardiopulmonary resuscitation (CPR) for providing feedback on the effectiveness of cardiac compressions. Currently, there are devices which can measure displacement distance, which is correlated to cardiac compression and induced blood volume changes. However, these devices do not directly measure the effectiveness of the compressions at inducing blood flow to the brain, which is the primary goal of CPR. The present invention can be applied to the head of a patient undergoing CPR, and direct readings can be made to detect the amplitude of the change in blood volume in the brain during CPR. In this embodiment of the present invention, the effectiveness of CPR can be monitored and improved by providing direct feedback to the CPR administrator as to the actual change in blood volume with each cardiac compression.

In addition to using the VIPS technology to produce a plethysmogram of intracranial fluid changes, the present invention also can be implemented using other technologies. For example, a plethysmogram can be generated using near-infrared spectroscopy (nirs), or by measuring the absorption of light at a variety of wavelengths. By way of example, pulse oximetry devices typically use two wavelengths of light and rapidly sample the absorption of those wavelengths during cardiac pulsations, creating a plethysmogram. This can also be accomplished with one wavelength. This type of light absorption technology can be applied to the brain, yielding a plethysmogram that can be used to evaluate shunt malfunction. A plethysmogram of the intracranial fluid can be created by a variety of technologies, and the present invention is not limited to any particular technical means of producing the plethysmogram.

In the art of ICP monitoring, skilled neurologists and other experts can examine the shape of the ICP plots and identify important clinical conditions. With a high sample rate, the plethysmogram produced by the present invention can produce a similar curve and can provide clinical practitioners with similar diagnostic information without the need for an invasive ICP probe. Information about arterial and venous blood flow and volume, intracranial compliance, edema, CSF volume and pulsation, can all be derived from a high resolution plethysmogram. In some cases, it may be useful to combine the VIPS plethysmogram with ICP monitors to better understand the patient's clinical condition, especially when information about multiple distinct fluids is needed. This technique can also be used to inform the clinician about intracranial compliance.

In another embodiment, detection of intracranial compliance can be accomplished by examining the changes in the volume of one or more intracranial fluids over time, or in response to an external stimulus, such as a valsalva maneuver, jugular vein compression, cerebrospinal fluid injection or withdrawal (as with a spinal tap), hyperventilation, hypoventilation, or change in patient position. The recovery after the initial stimulus can also be an indication of intracranial compliance and autoregulation. The present invention can be used in combination with an ICP monitor to establish the relationship between pressure and volume, and therefore provide information about intracranial fluid compliance and autoregulation. The present device could be combined with other monitoring technologies, such as, but not limited to, ECG, EEG, pulse oximetry, ultrasound, transcranial Doppler, and/or infrared SPEectroscopy, to spectroscopy to correlate intracranial fluid volume to other physiologic parameters that may be useful in diagnosing, managing or treating disease.

In another embodiment, the current device can be used to detect CSF leaks. For example, a patient who is at risk for a CSF leak, such as a patient undergoing a procedure with epidural anesthesia, could be monitored with the current device, and the device could alert the treating physician when there is a change in the volume of CSF. Since there is currently no way to directly detect CSF leaks during or following spinal or epidural anesthesia, the anesthesiologist will typically leave before the symptoms of the leaks become manifest, hours or days later. Because most patients are still in a recumbent position during immediate postoperative recovery, they generally will not experience any neurological symptoms until well after the surgery, when they stand up. Because of the depletion of CSF inside the skull, the brain will sag due to gravity and the absence of the normal buoyant force supplied by an adequate amount of CSF. It is commonly hypothesized that this sagging induces stress on some of the vessels supplying the brain, resulting in a severe headache, commonly known as a "spinal headache". One common treatment for this type of CSF leak, which is the result of an inadvertent dural puncture, is to inject the patient's autologous blood into the epidural space, near the puncture. This is called a blood patch. Other treatments involve injection of saline or other fluids into the space, or surgical repair of the dural tear. With the appropriate application of the current device, a novel method for treating patients can be formulated, comprising the following steps: applying an intracranial fluid monitor to a patient undergoing a procedure which may result in a CSF leak, detecting the CSF leak, and repairing the leak during the same operative session. Variations on this method could include detecting a CSF leak in a patient using an intracranial fluid monitor, and repairing the leak as a result of the leak detection. Or, a measurement of the intracranial CSF volume of a patient can be made prior to a procedure that may cause a CSF leak, and a second measurement of the intracranial CSF volume can be made during or after the procedure, and if a significant reduction has been detected, the repair can be made before the conclusion of the procedure. Alternatively, the second measurement can be made at any time after the procedure, and a repair can be made after the detection of the leak.

In another embodiment of the current invention, plethysmography is used to detect respiratory rate and volume, heart rate, or penile erectile function. For instance, sensors could be designed so that they would adhere to the torso in such a way as to detect the extent of thoracic excursion due to the breath cycle. Sensors could also be integrated into an arm band, ear phones, or a watch bracelet to monitor changes in blood volume of the underlying tissue that would then be related via mathematical transformations to the cardiac and respiratory cycles. Sensors adherent to the base of the penis could measure volumetric changes associated with erectile response.

The console of the VIPS system, according to one embodiment, may include a custom electronic device with a display. A laptop computer or tablet, such as an iPad, could alternatively be used. Using one of these off-the-shelf computers has the advantage of having already integrated wireless communications capability, including Bluetooth or WiFi. But custom consoles comprised of off-the-shelf or custom components can also be used.

In order to detect an asymmetry (or other symmetrical or non-symmetrical characteristics) of the fluids in the brain, multiple transmitters and receivers can be strategically located. The transmitters and receivers may be located such that the transmitters transmit through different portions of the bulk tissue of the patient and the receivers are located generally opposite to the transmitters so as to receive the signals through the tissue. For instance, a single transmitter (or receiver) could be located on or near the forehead of the patient, and two receivers (or transmitters) are spatially separated from one another and could be located on either side of the head, preferably toward the back, such that the time varying magnetic field propagates through each hemisphere, or in the case of two transmitters each of the time varying magnetic fields propagates uniquely biased to different sides of the brain. In this example, the magnetic fields received by the receivers (or in instances where two transmitters are used, the two magnetic fields received by the single transmitter) will be transmitted substantially through different portions (e.g., a first portion and a second portion) of the overall tissue sample. Depending on the orientation of the transmitter/receiver, there may be some overlap in the tissue portions, but generally the transmitters are arranged to be transmitted through discrete sections of the overall bulk tissue.

Continuing with this example, uneven signals between the two receivers and one transmitter, or one receiver and two transmitters, could be an indication that a stroke or hemorrhage was present on one side. This is useful, because most brain lesions are not directly in the center of the brain. So, detecting an asymmetry would be an indication of a lesion. To identify the signals sent from each of the transmitters, the signals may include a transmission characteristic as an identifier, such as a synchronization pulse, amplitude or frequency modulation, and or each transmitter could transmit at different fundamental frequencies or a different series of frequencies. For example, the signal sent from the first transmitter may have a different frequency from the signal sent from the second transmitter. As another example, the signal sent from the first transmitter may be shifted in time as compared to the signal sent from the second transmitter. As yet another example, each or one of the signals may include a bit of data (e.g., an amplitude value, or the like) that corresponds to the particular transmitter from which it was transmitted.

It is possible to allow a single antenna or coil to act as either a transmitter or receiver at different times, thus creating a transceiver. A switch could be implemented, to switch the antenna from being a receiver to being a transmitter and vice versa. For example, the use of a gallium arsenide FET or PIN diode switch could be used. Alternatively, two concentric loop antennas could be located on the same printed circuit board or other substrate.

In measuring phase shift, some of the electronic components can be sensitive to temperature changes. To minimize the effect of temperature-induced variation, it may be desirable to design the cable from the transmitter to the analog-to-digital converter to be the same length as the cable from the receiver. The addition of compensating electrical resistance or reactance in the form of series/parallel networks of resistors, capacitors, and inductors can also minimize the effect of temperature. Furthermore, heaters or thermo-electro-coolers and thermal insulation may be used to temperature stabilize amplifiers or other components that are inherently temperature sensitive.

To reduce the effect of the mismatch of the transmit antennae to the cable that delivers the RF transmit signal, a directional coupler may be used to remove cable reflections and provide a pure sample of the transmit signal that may be used for analog-to-digital conversion.

To reduce the sensitivity of the system to movement of people or other objects near the antennae or in the magnetic field, shielding of the antennae to direct the magnetic field may be useful. Various field shaping passive devices formed from ferrites, other magnetic materials, or electrical conductors may be incorporated with the antennae to best match the field profile to the human brain cavity.

Algorithms

As has been described, the VIPS device may capture electrical property data at a multitude of frequencies. This data may include measurements of the phase shift and attenuation of voltage or current signals between the emitter and detector. In some embodiments, there will be measurements of phase shift or attenuation between multiple emitters and detectors.

Different biological tissues have varying electrical properties and thus induce different phase shifts and attenuations. By examining the frequency response of the electrical property changes—e.g., phase shift—it is possible to examine volume changes of each of the types of fluid separately. Because the skull is a rigid and closed volume, changes to the volumes of different fluids, such as blood, intracellular fluid, extracellular fluid, and cerebrospinal fluid, affect each other, since the total fluid volume must remain essentially constant. The fundamental relationship between intracranial pressure and intracranial fluid volume was first published over two centuries ago by Professors Monro and Kellie. Monro and Kellie established the doctrine that, because the skull is essentially a rigid, closed volume, venous flow of blood out of the cranium is necessary to allow arterial blood flow into the cranium. This phenomenon also applies to other intracranial fluids.

A variety of algorithms can be generated to reliably detect changes to the intracranial fluids. Formulas may be derived from the phase shift, attenuation or other electrical parameters at certain frequencies for certain fluids. One formula, $B(p(f1), a(f2))$, may be empirically derived which is strongly correlated with intracranial blood volume. In the present example, the formula B, is a function of phase shift (p) at a particular frequency (f1) and attenuation (a) at the same or another frequency f(2). In live patients or animals, as blood volume increases, we would expect the volume of cerebrospinal fluid to decrease. Therefore, if we derive a formula for cerebrospinal fluid and call it C, then, a rise in the ratio of B/C may be a good indicator of venous blood pooling, or an intracerebral hemorrhage. As another example, it is well known that as cerebral edema develops, the increased intracellular and extracellular fluid volume pushes some of the intracranial blood out of the skull. Therefore, if we derive a formula for cellular fluid, and call it CF, then the ratio CF/B can be used as a metric to quantify edema. Using ratio formulas can be particularly helpful to divide out noise factors that may affect both the numerator and denominator.

Going further with this general method, many such algorithms may be developed, which take advantage of formulas which correlate strongly with one or more particular intracranial fluids and or location of the fluids in the brain's hemispheres. Relationship between two or more fluids can be expressed in mathematical formulas which may include ratios, products, sums, differences, or a variety of other mathematical relationships.

The present invention can be used to diagnose conditions, such as cerebral bleeding or edema. But it can also be used to help control the administration of treatments for some of these conditions. For example, the device could be used for measuring cellular fluid in brain tissue. In a case of dangerous edema, physicians will often administer intravenous drugs like mannitol and hypertonic saline solution to draw water out of the brain. If not administered properly and in the right dose, these drugs can be dangerous. For the treating physician, it would be useful to know how much fluid was removed from the brain tissue. Therefore the use of a device such as the one described here would have utility as a means for providing feedback for treatments to reduce intracranial fluid volume. Another example would be to use such a device to provide a measure of intracranial blood volume as feedback for administering drugs that alter blood pressure and flow rate, that are sometimes used to treat patients with brain injury. Other examples where intracranial fluid measurements could be used as feedback include: hydration during intense exercise such as running marathons; sodium concentration during intense exercise; or in treating patients with improper levels of sodium.

Although the examples used here are focused on intracranial fluids, algorithms and treatment methods using a device that can distinguish different types of fluids can be used in other fields of medicine as well. Algorithms and feedback techniques such as are described above can be used to reliably measure ratios of different types of fluids in other parts of the body. For instance examining the fluid that builds up inside the lung tissue in patients with congestive heart failure can be read as a change in the ratio of lung fluid to blood in the same region. Lymphedema that commonly occurs in the arms of patients after breast cancer surgery can be measured as a ratio of extracellular fluid to blood or muscle tissue volume. Treatments for patients that affect tissue fluid volume, such as compression garments for lymphedema, or diuretics for congestive heart failure patients, can be dosed using feedback as has been described above.

Clinical Applications

A number of clinical applications for the VIPS systems and methods are described above and will be described below. These examples are provided for illustrative purposes and are not intended to limit the scope of use of the VIPS systems and methods described herein. In fact, the VIPS systems and methods described in this application may have a large number of different uses and applications, in a number of different clinical settings, from in the field or emergency vehicle to the battlefield to the hospital to the nursing home, and the like. Therefore, the above and following descriptions should not be interpreted as limiting the scope of the invention as set forth in the claims.

One clinical application for the VIPS systems and methods described herein is hemodialysis. During hemodialysis, blood is withdrawn from a patient's vein, and substances including sodium and urea are filtered out. The blood brain barrier prevents these larger molecules, called osmoles, from leaving the brain quickly. This sets up a concentration gradient that provides osmotic pressure to draw water across the blood brain barrier into the brain, resulting in cerebral edema. In extreme cases, this cerebral edema causes a condition called dialysis disequilibrium syndrome and can be severe enough to cause degradation of brain function, or even permanent brain injury. Partly for this reason, dialysis is performed over a prolonged period of time, typically about 4 hours. It is believed that many patients could undergo a more rapid dialysis protocol, but it is difficult to ascertain which patients could tolerate the faster rate. A new dialysis protocol could be enabled by the VIPS system described herein, by monitoring the intracranial fluids during dialysis. The steps of this method would involve placing a fluid monitor on the patient prior to initiation of dialysis, initiating dialysis at a relatively fast rate, and checking for signs of cerebral edema. As edema progresses, the dialysis can be slowed in response to the fluid readings, thereby customizing the dialysis rate for each patient based on their ability to tolerate the process.

For patients with sodium imbalances, the VIPS system described herein may be used to detect changes to the sodium level that may result in conditions such as hypernatremia and hyponatremia. In patients suspected of such conditions, the system may be deployed to detect and diagnose the condition, or to aid the clinician in the treatment of the patient to correct their sodium balance by providing real-time feedback during administration of fluid or drug therapies.

The VIPS systems and methods described herein may also be used during heart surgery. During heart surgery, there is a risk that not enough blood is getting to the brain. This can be the result of an embolism or of lack of circulation or low blood pressure to the brain. One article that discusses this problem is "Silent Brain Injury After Cardiac Surgery: A Review" by Sun et al, Journal of the American College of Cardiology, 2012. A fluid monitor could detect a reduction in the amount of blood in the brain, and it could detect ischemia in the brain tissue. Thus, a new monitoring technique could involve placing a fluid monitor, such as the system described herein, on a patient at the beginning of a cardiac surgery and monitoring the patient during the surgery. In the event that the device detects brain ischemia or a reduction in the blood volume in the brain, the physician may be alerted and may attempt to correct the problem through a variety of clinical means.

A VIPS device can be configured to monitor intracranial pressure noninvasively. It is well known in the field of neurology that intracranial pressure and volume are approximately linearly related when the intracranial fluids are properly regulated by the body's own intracranial fluid control systems. It has been established in clinical studies that a VIPS device can detect fluid shifts that are proportional to pressure changes.

There is a need for detecting ischemia in the G.I. tract, especially in neonates. The VIPS system described herein may be used to detect such G.I. tract ischemia, either with continuous monitoring or with instantaneous measurements.

Prevention and detection of head injuries in automobile accident victims, in football players, in the military, and in other types of head injuries is a critical need. Accelerometers have been added to football helmets to monitor accelerations due to impact, and companies like Nike, Inc. have acceleration detectors integrated into caps. But accelerometers are, at best, an indirect way to help determine likelihood of head injury. It is the movement of the brain within the skull in response to the external acceleration forces that leads to concussion or brain injury. In one embodiment, a VIPS device could be added to (or incorporated into) helmets, caps, headbands, or applied directly to the head, and could detect the movement of the brain within the skull during the impact. This could be used instead of accelerometers, but would be most effective if used in conjunction with accelerometers. Monitoring brain movement within the skull with VIPS would provide a better measure of potential for brain injury than accelerometers alone. Football is one application. Crash testing is another. Research in vehicle safety could benefit greatly from a better understanding of brain movement during impact (e.g., crash testing with cadavers monitored with VIPS).

Detection of concussion is important, especially in sports injuries. If a person has a concussion, a second concussion before the first has resolved can result in a very severe injury called second impact syndrome. ("Second Impact Syndrome", Bey & Ostick, West J Emerg Med. 2009 February; 10(1): 6-10.) Although the science of concussion and its effect on intracranial fluids is still evolving, VIPS could be used to detect early stages of intracranial swelling, hyperemia, venous pooling, hemorrhage, ischemia, blood flow rate changes, and/or other biologic changes affecting the tissue's bioimpedance. With a VIPS device, readings may be taken prior to a game or at some other baseline time, and readings after a potential injury event may be compared to the baseline to establish the presence or degree of injury.

A variety of other medical conditions may be monitored with the VIPS system described herein. Peripheral edema can be caused by a variety of medical conditions. Swelling in the feet and legs is common among patients with congestive heart failure. Swelling in the arms is common after breast cancer surgery when patients develop lymphedema. Swelling is common in limbs or other parts of the body after surgery. In some types of surgery, there is a flap of tissue that is at risk for ischemia, edema, or venous pooling. Compartment syndrome can result after an injury when there is insufficient blood flow to muscles and nerves due to increased pressure within the compartment, such as an arm, leg, or any enclosed space within the body. Current devices measure compartment syndrome pressure using a needle to penetrate the tissue and take a reading of the pressure. ("Accuracy in the Measurement of Compartment Pressures: A Comparison of Three Commonly Used Devices", Boody & Wongworawat, J Bone Joint Surg Am. 2005 November; 87(11):2415-22.) Patients with congestive heart failure or other conditions can have a buildup of fluid in their lungs or chest cavity. The VIPS device described herein may be used to monitor changes related to swelling, blood flow, perfusion, and/or other fluid characteristics of limbs and other parts of the body due to any of these or other conditions. A baseline reading may be taken, and subsequent measurements may be compared to that baseline to monitor and detect changes, for example, to swelling or perfusion of the tissue. Continuous monitoring of swelling may provide feedback for medical therapies to control edema, blood flow, or other clinical parameters.

Dehydration can be a life-threatening medical condition and can occur during athletic activities, such as marathon running, and in patients with a variety of medical conditions. The VIPS device described herein may be used for quantifying the hydration level of a patient for purposes of an initial diagnosis, for monitoring effectiveness of treatment, and/or as an alarm to a worsening condition of a patient.

Fighter pilots and other people undergoing extreme accelerations can sometimes lose consciousness, as a result of sudden fluid shifts within their brain. Similar conditions can occur in deep sea divers, astronauts, skydivers and mountain climbers who are exposed to extreme conditions that may affect their intracranial fluids. The VIPS device described herein may be installed inside a helmet or otherwise affixed to a person's head during activities that put them at risk for changes to their intracranial fluids could be monitored in real time. If a dangerous change in fluids were to occur, the individual or a third party could be alerted to provide intervention.

Migraine headaches are well known to be caused by expansion of blood vessels in and around the brain. Regular or continuous monitoring of intracranial blood volume may be used to diagnose or better understand the physiology of migraine. An individual migraine patient may quantify the effect of various migraine treatments during administration, and may use that information as feedback to titrate medication or otherwise adjust therapy. Regular periodic monitoring by migraine patients, for example brief VIPS spot check readings nightly and upon waking in the morning, would allow individuals to detect characteristic intracranial fluid changes that precede migraine headache symptoms, thus facilitating earlier interventions that more effectively reduce symptoms.

Penile plethysmography is commonly used in urologic surgery to evaluate erectile function before and after prostate resection. Currently, this is typically accomplished via circumferential strain-gauge transducers. A VIPS sensor could be used to provide direct volumetric measurements of penile filling. Such a device could also be used in the ambulatory setting to evaluate the etiology of erectile dysfunction, i.e. whether physiologic or psychogenic, or monitoring nighttime arousal.

As described above, various methods using the VIPS systems 100, 700 to detect bodily fluids (either directly or indirectly) may be used. For example, in one method, asynchronous EKG and VIPS readings may be time-stamped, and the VIPS readings may be binned as a function of position in the cardiac cycle for subsequent analysis. Exemplary analysis includes, for example, statistics such as median or mean values in each bin. Differences between mean values for bins associated with diastolic and systolic portions may indicate the extent of fluid exchange. As another example of a method, a signal processing algorithm (e.g. FFT, DFT) may be applied by the processing unit 104 and/or computing device (e.g., laptop, desktop, server) to the measured phases, amplitudes, and/or weighted combinations, such as the computed indicators that correlate with blood, CSF, etc., in order to determine heart rate (a frequency) and/or amplitudes of fluid changes associated with the cardiac cycle.

Physiologic monitoring is commonly used in a variety of medical settings, with physiologic parameters including heart rate, respiratory rate, blood pressure, oxygen saturation of the blood and the like. While a variety of modalities currently exist to derive these values—electrical, optical, and others—VIPS may also be used to provide data on some or all of these vital signs, thereby obviating the need for additional monitors when a VIPS device is already being used for cranial fluid surveillance, or as an additional source of the same information. In one embodiment, for example, a physiologic sensor may be used to detect, either directly or indirectly, one or more characteristics of fluid flow or other conditions within the patient's body, and then these conditions may be used to calibrate or filter the data from the VIPS system.

Autoregulation of intracranial fluids is a complex biological process, involving vasodilation, vasoconstriction, movement of cerebrospinal fluid (CSF) between various compartments of the brain and the spinal column, and production of CSF. Patients with a variety of neurological disorders can have poor autoregulation, which can lead to elevated or reduced intracranial pressure. The VIPS device described herein may be used to evaluate the autoregulation and intracranial compliance of a particular patient. Tests may be developed to measure the fluid changes that occur as a result of a procedure or posture change. For example, a patient may lie flat on his or her back, and a clinician may take a fluid volume reading, raise the patient's legs into an elevated position, and measure the fluid changes that occur. Other tests may include intravenous infusion of bulk fluids, administration of medications, and/or moving the patient from a flat to vertical position, all of which may induce a change in the blood, CSF and other fluids in the brain. The results from a particular patient test may be compared against a baseline measurement of the same patient performed at a different time, or against a database of known normal and pathologic responses, helping the clinician to better understand the patient's autoregulation and intracranial compliance status. With a better understanding of a patient's intracranial fluid function, the clinician may be better able to select a course of treatment that is most beneficial to the patient.

Studies comparing the return to normal cerebrovascular reactivity (CVR) in subjects after voluntary manipulations of the blood flow to the brain show a difference between those with a concussion and healthy subjects. Unlike healthy subjects, those with concussions failed to return to normal CVR after hyperventilation tests. This condition lasted for several days after the concussion. In contrast, in healthy subjects, the CVR returned to normal conditions in a much shorter time. The experimental example described below demonstrated that bulk measurements of the electromagnetic properties of the brain may have measurable changes during tests that affect CVR, such as the Valsalva maneuver and jugular vein compression. The results show that return to both temporal and magnitude normal can be detected precisely with the devices and methods described in this patent application. This illustrates that the devices and methods can be used to detect a variety of diseases, such as concussion, by evaluating the temporal and magnitude patterns of the excursion from a normal signature, due to maneuvers that produce well-controlled voluntary changes in blood flow.

EXPERIMENTAL EXAMPLE

This experiment was based on the idea that substantial insight can be found in the electromagnetic signature response to a voluntary change in tissue condition. This could lead to a much more controlled diagnostic method, based on electromagnetic measurements of biological tissue condition. In one experiment, a voluntary change was produced in the interrogated organ or tissue, and the diagnostics were performed by evaluating the changes of electromagnetic properties that occurred in those organs or tissue in response to the voluntary produced change and correlating these changes to the voluntary action.

One example of the method relates to brain concussion, an important medical problem in sports medicine. Sports induced concussion or mild traumatic brain injury (mTBI) is of increasing concern in sports medicine. Neuropsychological examination is the main diagnostic tool for detecting mTBI. However, mTBI also produces physiological effects that include changes in heart rate and decreases in baroreflex sensitivity, cellular metabolism and cerebral blood flow.

Cerebrovascular reactivity (or "cerebrovascular response," CVR), which is a measure of cerebrovascular flow, is impaired by brain trauma. Various methods are used to assess CVR. They include hyperventilation, breath holding, $CO_2$ inhalation, and administration of acetazolamide. It has been shown that Doppler ultrasound measurements on the carotid artery can be used to monitor changes in CVR, which can then be correlated with mTBI and used for diagnosis of the condition. The methods and devices described herein provide an alternative means for measuring changes in CVR, with a practical application in diagnosis of mTBI.

This experiment demonstrates that the various methods used to assess CVR through voluntary actions on the body produce changes in the electromagnetic properties of the brain. These properties produce a distinct signature in magnitude and time and can therefore be used with our device for brain diagnostics.

Experimental System: Inductive Spectrometer

An experimental multi-frequency inductive spectrometer was designed and constructed. The system consisted of four modules: function generator, transceiver, dual-channel demodulator and analog-digital converter. A personal computer was used to control the system and process the data. The function generator module used two identical programmable synthesizers (NI 5401 synthesizers, National Instruments, Inc., Austin, Tex.) as oscillators. The first oscillator supplied an excitation signal I $\cos(\omega_e t)$ of approximately 20 mA, in the range of 1 to 10 MHz, at pre-programmed steps. A modulation signal I $\cos(\omega_{mt})$ was generated by the second oscillator. The difference $\omega_e - \omega = \omega_0 = 100(2/\pi)$ was maintained constant in the whole bandwidth, in order to produce a narrow band measured voltage signal on a constant low intermediate frequency for processing and demodulation.

The excitation and modulation signals were connected to the transceiver and the dual-channel demodulator modules, respectively. The transceiver consisted of an excitation coil and a sensing coil, coaxially centered at a distance d=18 cm and two differential receiver amplifiers AD8130. Both coils were built with magnet wire AWG32 rolled on a cylindrical plastic former with radius r=2 cm, five turns. The coil inductance, as calculated from Faraday's law, was approximately 40 mH. The excitation coil generated a primary oscillating magnetic field. The sensing coil detected the primary magnetic field and its perturbation through a proximal conductive sample. To avoid inductive pickup, the leads of the coils were twisted. The amplifiers were connected as conventional operational amplifiers and collected the reference voltage ($V_{ref}$) and the induced voltage ($V_{ind}$) in the excitation and sensing coils, respectively. The gain of the amplifiers was adjusted in order to obtain a dynamic range of ±5V throughout the whole bandwidth.

The dual-channel demodulator module used a mixer and a narrow band pass filter to transfer the information of any excitation and sensing frequency to the same low frequency ($\omega_0$). This module used two similar channels for demodulation of the reference and induced signals. To avoid additional inductance and stray capacitance in the circuit, the amplifiers and dual channel-demodulator circuits were shielded by a metallic box and connected to the coils with short coaxial cables (length less than 0.8 m). The current passed through the shield to minimize any inductance mutual between the circuit and the coils.

The analog-digital conversion module digitized the reference and induced voltage signals on the constant low frequency. A data acquisition card (NI 6071E, National Instruments, Inc., Austin, Tex.), with a sample rate of 1.25 MSamples/seg and a resolution of 12 bits, was used as an analog-digital converter.

The phase of the reference and induced voltages are calculated in software over approximately five cycles by an extract single tone function available in LABVIEW V6.1 (National Instruments, Inc., Austin, Tex.). The phase shift between the reference and induced voltage was estimated as $\Delta\theta = \theta(V_{ref}) - \theta(V_{ind})$. The ratio signal to noise (SNR) for phase shift measurement was improved by averaging over twenty spectra (39 dB at 1 MHz).

Experimental Protocol:

External Jugular Vein Compression

The two external jugular veins, found on both lateral sides of the neck, are one of the main routes for cerebral venous drainage. By applying light pressure to both sides of the neck, a person can inhibit drainage. In doing so, intracranial fluid volumes increase 20-30 cc. The purpose of this experiment was to evaluate the ability of the phase shift intracranial fluid monitoring device, as described in this patent application, to detect these changes in blood volume.

The experiment showed that, following release of the jugular vein after compression, there was an exponential decay in reading. It also showed that, following a second compression and release, the reading did not return to the original value. This is typical of CVR when the metabolism is exhausted due to partial ischemia. It suggests that this method can provide another technique for evaluating CVR and thereby assess concussion.

Figure 12:
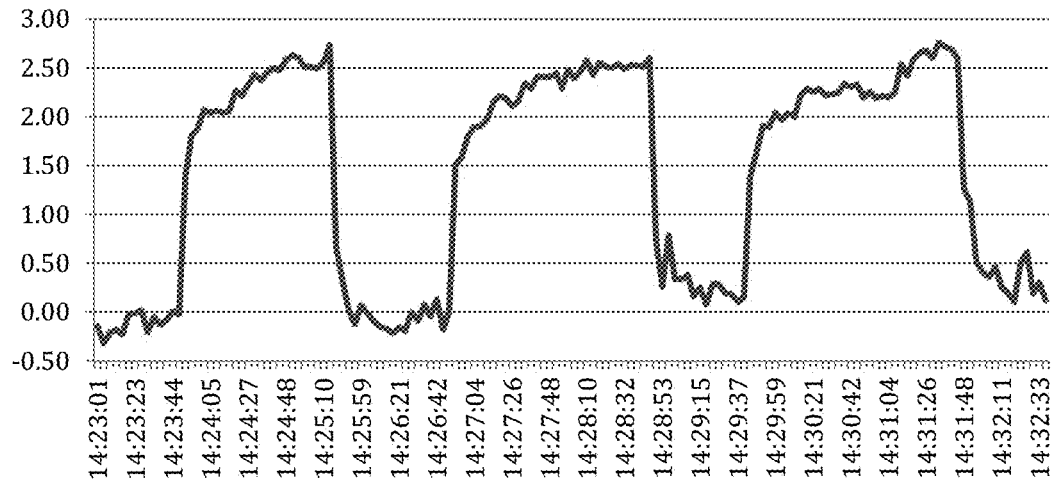
FIG. 12 is a graph illustrating calibrated phase shift measurements as a function of time, according to one embodiment.

With reference to FIG. 12, the results of the experience are presented in the graph. As shown in FIG. 2, calibrated phase shift measurements are plotted as a function of time and the increase in phase shift is caused by the vein compression and the decrease during the release. Further, following the blood vessel release there is an exponential decay in reading that does not return to the original value. This is typical of CVR when the metabolism is exhausted due to partial ischemia and indicates that the method can provide another technique for evaluating CVR and assessing concussion.

Valsalva Maneuver

The Valsalva maneuver is performed by moderately forceful attempted exhalation against a closed airway, usually done by closing ones mouth and pinching ones nose while pressing out, as if blowing up a balloon. The Valsalva maneuver tests the body's ability to compensate for changes in the amount of blood that returns to the heart (preload) and affects the blood flow into and from the head. The dynamic response of the circulation system through the maneuver is indicative of several physiological functions, including the CVR. There are other conditions that can be evaluated with this procedure. For instance, patients with autonomic dysfunction will have changes in heart rate and/or blood pressure that differ from those expected in healthy patients.

A temporal response to the Valsalva maneuver was measured, using a device as described herein. The measurement had several typical temporal aspects that may be used for diagnostic purposes. These include the time constant of the increase in the reading, the peak value, the time constant of the decays, and the final short term and long term values.

Figure 13:
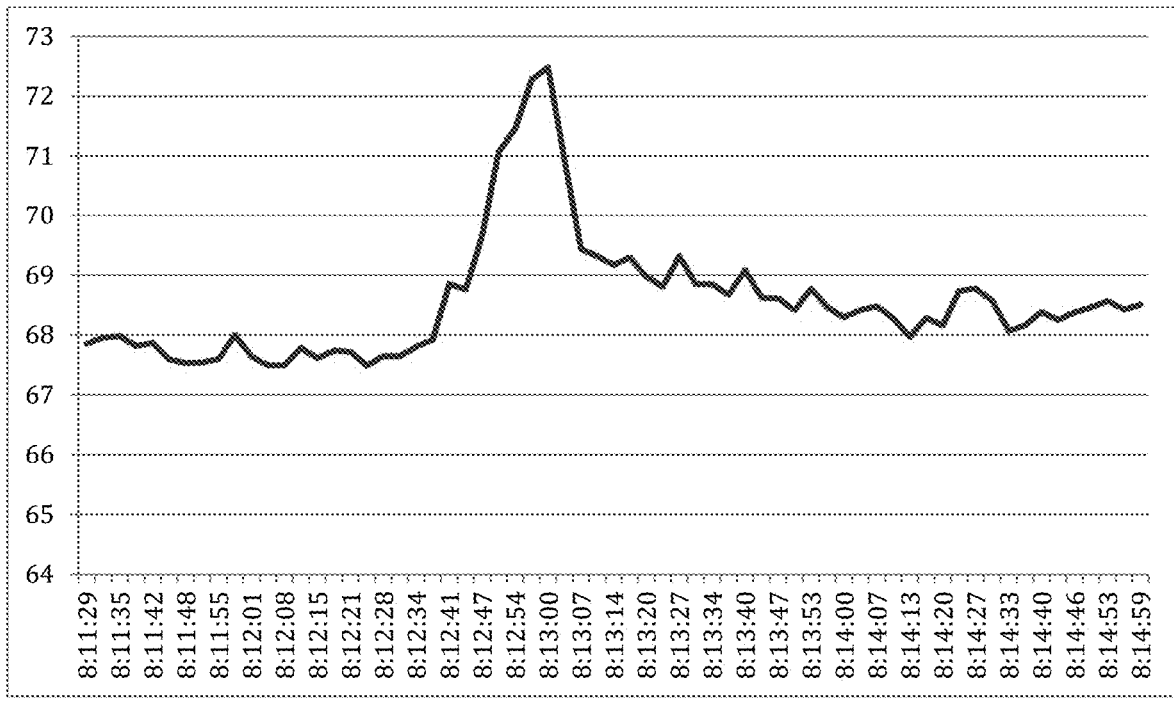
FIG. 13 is a graph illustrating changes in phase shift reading as a function of time during application of the Valsalva procedure, according to one embodiment.

FIG. 13 illustrates a graph shown the changes in shift reading as a function of time during the Valsalva procedure. As shown in FIG. 13, the reading has several typical temporal aspects that can be used for diagnostics and these include the time constant of the increase in reading, the peak value, the time constant of the decay, as well as the final short term and long term value.

Detecting Concussions

Return to normal CVR in subjects after voluntary manipulations of the blood flow to the brain is different for those with a concussion than it is for healthy subjects. Subjects with concussions failed to return to normal CVR after hyperventilation tests for several days after the concussion. In healthy subjects, on the other hand, the CVR returned to normal conditions in a much shorter timeframe. Our experiment shows that our bulk measurements of the electromagnetic properties of the brain show measurable changes during tests that affect the CVR, such as the Valsalva maneuver and jugular vein compression. The results show that return to normal can be detected precisely with our measurements. This proves that our device can be used to detect a variety of diseases, such as concussion, by evaluating the temporal and magnitude patterns of the excursion from a normal signature due to maneuvers that produce well-controlled voluntary changes in blood flow.

Detecting Large Vessel Occlusions

Almost 50% of ischemic strokes are clinically referred to as either cerebral thrombosis or cerebral infarction. These strokes fall into two categories: small vessel occlusions (or "thrombosis") and large vessel occlusions (LVO). Large vessel occlusion occurs when there is a blockage in one of the brain's larger blood-supplying arteries, such as the carotid, middle cerebral, or basilar arteries. Small vessel occlusion involves one of the brain's smaller and deeper arteries. The effect of an occlusion of one or more cerebral blood vessels is reduction or elimination of arterial, oxygen rich blood flowing beyond the occlusion, resulting in hypoxia in (i.e., insufficient oxygen delivery to) "downstream" brain tissue. If undetected and therefore untreated, an LVO will result in brain cell death, causing lasting brain damage and in some cases death. If detected, arterial recanalization may be performed, to allow blood to flow again to the parts of the brain that were blocked from blood flow by the occlusion. Two methods for recanalization are intravenous (IV) thrombosis with tPa (tissue plasminogen activator) and mechanical recanalization. One of the main challenges in treating an LVO is detecting the LVO early enough to be able to provide effective treatment.

Earlier detection of LVO would result in earlier clinical intervention and therefore minimize brain cell damage. The ability to continually, non-invasively monitor for evidence of LVO may eliminate the need to keep the patient awake, may reduce or eliminate the need for hospital staff to perform continual visual monitoring and interaction with the patient, and may limit the patient's exposure to radiation from multiple CT (computed tomography) scans. Additionally, in some cases, LVO is actually a secondary brain injury, which may occur hours or days after the primary brain injury. The ability to monitor brain injury patients for secondary LVO, especially while they are asleep, is critical to improving outcomes.

Any of the embodiments of noninvasive, diagnostic, VIPS systems and methods described above may be used to monitor changes in fluids in the brain or other parts of the body to detect LVO. In any given case of LVO, there may be a detectible change in the fluid in the region of the brain affected by the LVO after the occlusion has occurred. Thus, one way to detect LVO is by monitoring a patient's cerebral fluid(s) over time and watching for changes that would indicate a possible LVO. Such a detection method may involve either multiple "snapshots" of fluids over time or continuous monitoring, according to various embodiments. As LVO persists, brain cells begin to die, due lack of perfusion, which results in edema and swelling. This edema and swelling may be detected using the VIPS systems and methods described in this application.

Another way to detect an LVO is to take just one "snapshot" of the brain, using a VIPS system as described herein, and compare blood volume in the right hemisphere of the brain with blood volume in the left hemisphere of the brain. In the event of an LVO on the right side of the brain, for example, there will be less blood on the right side than on the left side, thus indicating a likely LVO on the right. This method of detection can be performed instantly, and one advantage of this method is that it does not require a baseline fluid measurement for comparison. Therefore, this "single snapshot" method may be performed in a number of different settings, such as an ambulance or emergency department, to quickly detect an LVO. It may also be used in the hospital setting, for example to quickly detect a second stroke in a patient who earlier suffered a first stroke. Of course, for some patients the two methods of LVO detection may be used together—i.e., the monitoring of fluids over time and the single snapshot method. The VIPS systems and methods described herein allow for any combination of such methods to be applied to any given patient.

Although these techniques are being described here for use with LVO detection, they may have other applications for stroke detection as well. For example, in some embodiments, the techniques may be used to detect small vessel occlusions or hemorrhagic strokes, such as those caused by ruptured aneurysms.

Figure 15:
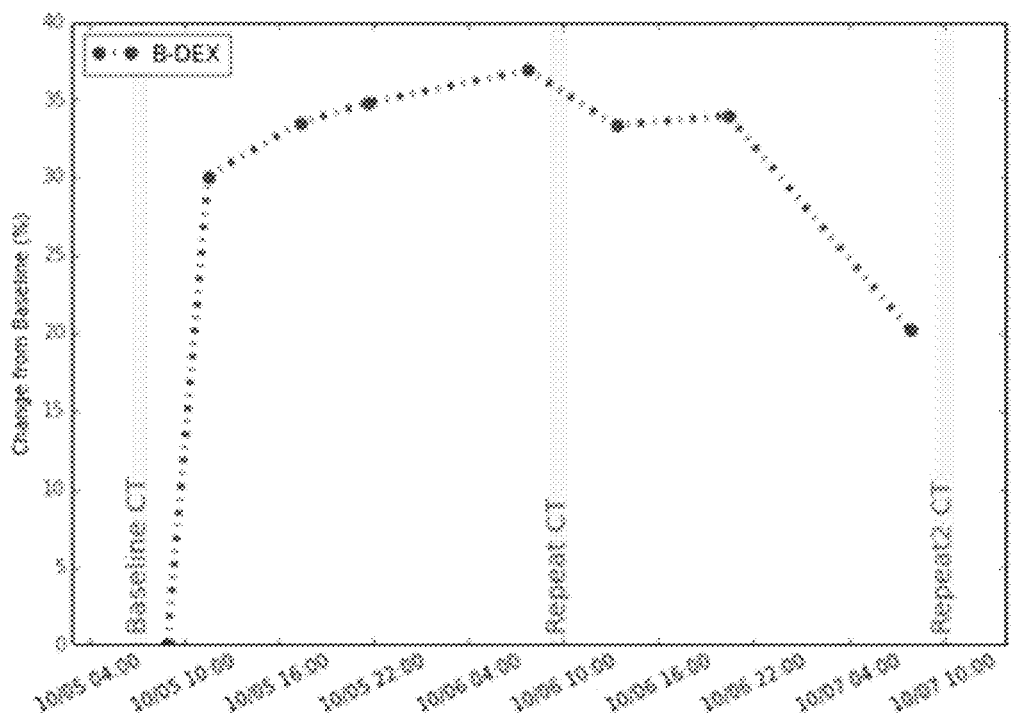
FIG. 15 is a chart illustrating measurements of a patient's cerebral fluid volumes over time, after a treatment of a cerebrovascular occlusion was performed.

Referring now to FIG. 15, detection of occlusion removal may also be important in patient management. After a successful recanalization (e.g., mechanical or intravenous tPa), cerebrovascular reactivity will occur, which will impart a fluid change as the blood rushes into the depleted arterial vascular system. Over time, the fluids in the brain (blood, edema, parenchymal fluid, etc.) will reach homeostasis, thus providing additional clinical feedback on effectiveness. Again, any of the VIPS systems and methods described herein may be used for detecting fluid changes associated with removal of a cerebrovascular occlusion. As detailed in this application, VIPS systems may also be used to identify one or more types of fluid in the brain, such as blood, CSF, edema, etc. FIG. 15 illustrates one clinical example of using a VIPS system as described herein to monitor a patient undergoing occlusion removal. Each of the dots on the chart represents one snapshot measurement of fluid volumes in the brain, using a VIPS system as described herein. The first dot, to the far left and at the bottom of the chart, represents a baseline measurement. The second dot (i.e., the next dot to the right from the baseline) represents the change in measured fluid volumes immediately after the occlusion removal procedure was performed. Subsequent dots, moving to the right on the chart, represent follow-up VIPS fluid measurements, showing a slower rise and then a tapering off of fluid volumes. This is but one example of a way in which a VIPS system as described herein may be used to measure fluid changes after an occlusion removal procedure.

In addition to detecting the presence of an LVO, the VIPS systems and methods described herein may be used to help determine where an LVO is located within the cerebrovasculature. Determining where the LVO is located, such as which hemisphere of the brain it is located in, may provide important clinical diagnostic feedback for preferential treatment. For example, a VIPS device with two transmitters and one receiver spatially separated to discriminate fluid changes in a particular region of the brain may be used to detect the hemisphere in which there is a fluid change. As mentioned above, this method may be used to detect the presence of the LVO, and it may also be used to help locate the LVO in the brain. The ability to determine whether an occlusion or other pathology is located in the right hemisphere or the left hemisphere is important beyond LVO conditions. Additionally, it may be possible in other embodiments to determine a location of an occlusion or lesion in other anatomical areas of the brain, vasculature or the like.

Bilateral Detection

Whether for use in locating LVO or for other applications, the ability to spatially detect fluid changes in the right hemisphere versus left hemisphere can be critical in the diagnosis and care of a patient. For example, determining what type of stroke has occurred—ischemic versus hemorrhagic—and which hemisphere it occurred in, provides crucial information to a clinician for administering an appropriate therapy. The ability to detect the plethysmograph (measure changes in volume in an organ) of the brain is useful beyond determining the patient's heart rate. For example, it may be used in detecting carotid artery stenosis, where the blood flow on one side of the brain is restricted versus the other. This could result in different plethysmograph amplitudes, thus providing clinically relevant information. It may also be used in detecting acute ischemic stroke (stenosis, thrombosis, infarction), which may lead to detection of a difference in plethysmograph amplitudes. In some cases, a hemorrhagic event in one hemisphere may attenuate the plethysmograph amplitude on one hemisphere only, thus providing additional clinically relevant data. The ability to detect "non-symmetry" in the plethysmograph information can provide critical clinically significant feedback for appropriate intervention.

VIPS technology has been previously discussed and disclosed as "volumetric integral phase-shift spectroscopy". This technology is based on the principles of spectroscopy, in that it generates and directs a spectrum (a range) of frequencies toward a part of the body (for example, chest or brain) and measures/detects the effect (for example, absorption and/or propagation phase delay) of the electromagnetic radiation due to the matter within the body part (for example, fluids). However, within this application, the concept of the generation and detection of a single frequency, and not a spectra or spectrum, is also disclosed. Furthermore, the acronym VIPS is used as "VIPS technology", "VIPS system", and the "VIPS device", for example, and VIPS in this context can represent a single frequency or spectra/spectrum/range of frequencies.

As described throughout this application, in many embodiments, multiple frequencies, phases and/or magnitudes may be used to measure fluid changes in a bodily organ or portion of the body, such as the brain, using VIPS technology (volumetric integral phase-shift spectroscopy). The focus of the above description, in fact, is on the use of multiple transmitters and/or receivers in a system, often used to distinguish between different types of fluid in a given space. In some embodiments, however, the systems described herein may use only one frequency, phase or magnitude to make any of a number of types of measurements. Plethysmography, as mentioned immediately above, is the measurement of changes in volume in an organ or a whole body, usually resulting from changes in blood or air volume. In some embodiments, the systems described herein may use one frequency to measure changes in blood volume in the brain or cranium to determine whether, for example, one hemisphere of the brain is receiving less blood flow than the other hemisphere. Similarly, one frequency may be used to measure overall changes in blood flow to the brain. This is but one example, which is provided to illustrate that although the description in this application focuses on the use of multiple frequencies, phases and magnitudes, some embodiments may employ only one frequency, phase and/or magnitude.

Figure 14:
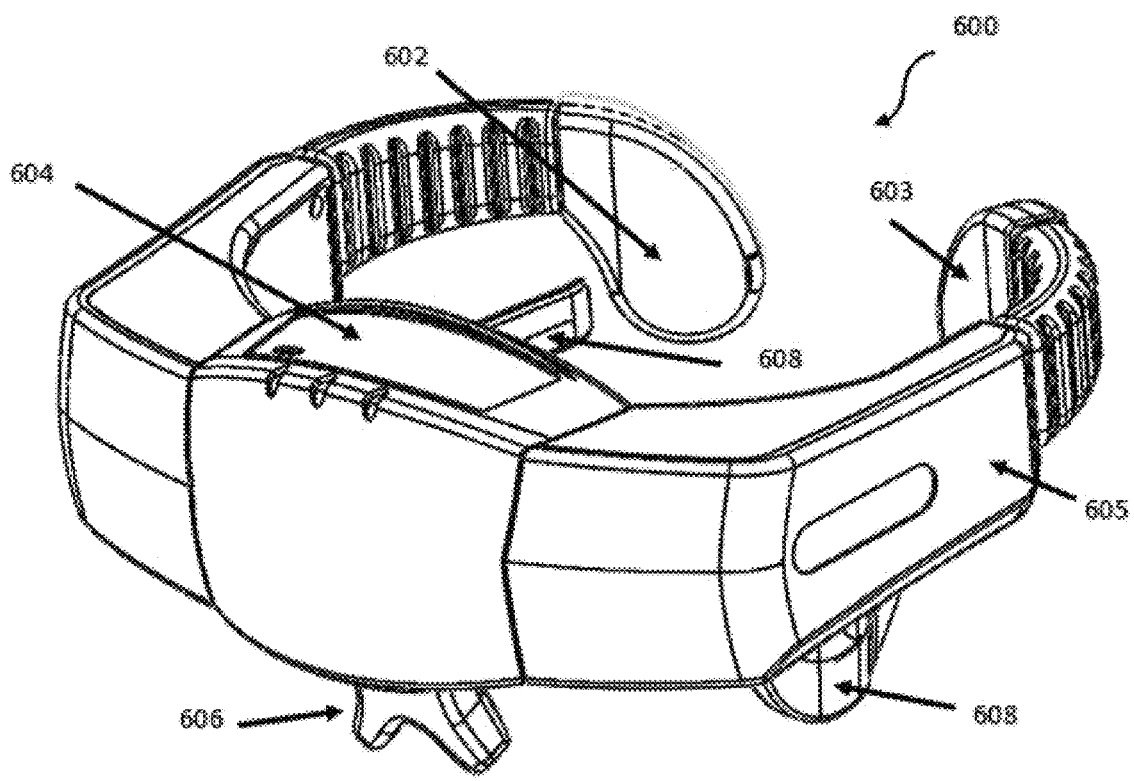
FIG. 14 is a perspective view of a headpiece for monitoring fluid changes in a body, according to an alternative embodiment.

FIG. 14 illustrates one embodiment of a headpiece 600 for use in a fluid monitoring system that may provide bilateral detection as described above. The headpiece 600 includes a frame 605, extending out to two wrap-around ends 602, 603. Each of the wrap-around ends 602, 603 contains a transmitter, and each transmitter preferentially transmits through one hemisphere of the brain to one or more receiving antennae in the headpiece 600. The wrap-around ends 602, 603 are also designed to wrap around the back of a patient's head, to help hold the headpiece 600 snugly onto the head.

The frame 605 also includes a housing 604, which houses controlling circuitry for the headpiece 600 and at least one receiving antenna. Two holding arms 608 may also be coupled with the frame 605, to rest on the patient's ears and thus help hold the headpiece 600 onto the patient's head. A nosepiece 606 may also be coupled to the frame 605, to provide a surface for the headpiece 600 to rest on the patient's nose and thus provide additional stability, as well as a consistent alignment/registration reference for subsequent placements of the headset 600 on the patient.

In alternative embodiments, other devices illustrated and described farther above may be used (or modified for use) in bilateral detection. The headset 600 described here is provided for exemplary purposes only.

Detecting and Differentiating Stroke

As mentioned above, various VIPS system and method embodiments described herein may be used for detection of stroke. Although some of the description above focuses on the detection of LVO (large vessel occlusions), the systems and methods described in this application may be used for detection of any type of stroke and/or for helping diagnose what type of stroke has occurred in a given patient. The following description provides further detail on this application of the VIPS technologies and methods described herein.

There are two primary stroke classifications—ischemic stroke and hemorrhagic stroke. Ischemic strokes are caused by arterial blockages or occlusions, while hemorrhagic strokes are caused by one or more ruptured blood vessels, leading to bleeding inside the cranium. The clinical pathway for treatment of a stroke is driven by whether the stroke is ischemic or hemorrhagic. In the case of an ischemic stroke, for example, tissue plasminogen activator (tPA) may be administered to dissolve blood clot(s) causing the stroke, or surgical intervention may be used to mechanically remove the blockage(s). In the case of a hemorrhagic stroke, on the other hand, drugs may be administered to reverse the thinning of the blood and encourage clotting, or surgical intervention may be required to suture the rupture. These are only examples of types of stroke treatment, but they illustrate the fact that the type of stroke typically dictates the type of treatment.

Time is critical in the treatment of the stroke, regardless of which type of stroke has occurred. This is because the stroke "starves" the affected area of oxygenated blood, resulting in brain cell death. If a clinician can (1) ascertain the hemisphere of the brain in which the stroke has occurred and (2) determine the type of stroke, using a non-invasive, portable medical device, clinically significant data will be provided much sooner than current methods for confirmatory diagnosis.

For example, when a stroke victim is picked up by an emergency medical technician (EMT), precious time has already lapsed. Once the EMTs arrive, they do not have a medical device to determine what type of stroke has occurred, and thus they are not able to administer the appropriate treatment, such as tPA for an ischemic stroke. Further delays occur due to the need for transporting the patient to a medical facility. Once at the facility, the patient will be sent for a computed tomography (CT) scan—the diagnostic standard of care—to determine which hemisphere the stroke has occurred in and what type of stroke has occurred. With these data, the clinician can administer the appropriate treatment. If, however, the EMTs were able to ascertain the type of stroke and which hemisphere it occurred in at the point of first contact, they could make educated treatment decisions much earlier for the patient. For example, the EMT might know to administer an appropriate drug and/or to direct the patient to a stroke center rather than a primary hospital. This is a well-known need, and some ambulances are now being equipped with mobile CT machines to allow diagnosis in the ambulance. Equipping ambulances with CT machines, however, is expensive and difficult.

The noninvasive, diagnostic, VIPS systems and methods described above may be used to monitor changes in fluids in the brain to detect the occurrence of a stroke and help differentiate the type of stroke. This technology takes advantage of the fact that most strokes occur in only one hemisphere of the brain, and the left and right hemispheres of the brain are separated by the medial longitudinal fissure. In the event of an ischemic stroke, an occlusion blocks the flow of blood to tissue, resulting in tissue ischemia, or less blood in the tissue. In the event of a hemorrhagic stroke, a blood vessel ruptures, allowing blood to flow out of the vessels, forming a hematoma. There is also reduced blood supply downstream from the rupture. The VIPS monitors described herein measure fluid volume, volume change from a baseline, and/or the plethysmograph caused by the heart stroke volume per beat. This VIPS technology is also configured to uniquely measure different volumes in a given region, which provides the ability to detect symmetry, non-symmetry, and bulk volumes/measurements. (The term "bulk," as used herein, means overall, as opposed to a measurement of only fluid volume, only solid volume or the like. "Bulk" is not intended to imply any certain amount or a large amount.)

As described above and in relation to FIG. 14, the VIPS technology can be configured to uniquely measure the brain's right versus left hemisphere. For each stroke type different frequency responses of phase shifts, attenuation and/or other electrical properties may be measured with the described VIPS technology. Algorithms may be used to uniquely identify, for example, the particular correlations to changes in blood volume (increase or decrease) and/or changes in plethysmograph responses. The ability to discriminate left versus right hemisphere volume or fluid changes (symmetry versus non-symmetry) can also be incorporated into an algorithm to further enhance the identification of which hemisphere and the type of stroke. In the case of an ischemic stroke, blood volume decreases in the hemisphere where the stroke has occurred, whereas the opposite side's volume remains relatively constant. In the case of a hemorrhagic stroke, extravascular blood volume will increase in the hemisphere of occurrence, and tissue blood volume (intravascular) may decrease, whereas the opposite side's volume remains relatively constant. In both cases, the VIPS monitor may be used to measure a bulk volume change (or a change in fluid volume) from a baseline measurement and/or non-symmetry in right hemisphere vs. left hemisphere bulk volume (or fluid volume), thus detecting the occurrence and/or progression of a stroke. With changes in blood volume, there will be a change in the plethysmograph response. For example, when there is a large vessel occlusion (large ischemic stroke), the tissue downstream from the occlusion will not pulse with blood with each cardiac cycle, reducing the amplitude of the cardiac plethysmogram measured by the VIPS device in the affected hemisphere. An algorithm employed in such a device may be used to examine the ratio or difference in the plethysmograph amplitude to detect a large vessel occlusion and diagnose an ischemic stroke.

Detecting Asymmetry

As described at several points above, the VIPS systems and methods, such as the headpiece 600 of FIG. 14, may be used to detect asymmetry (or "non-symmetry") in the cranium of a patient. Various examples of this are described above. More generally, however, the headpiece 600 or other embodiments of the VIPS system described herein may sometimes be used to simply detect asymmetry in the head. This asymmetry may be an asymmetry of fluid, solid, tissue, combination of fluid and solid, shape, signal intensity, movement of a substance within the head, or any other asymmetry. The asymmetry may also be in any direction within the head and may compare any two or more portions of the head. In one embodiment, for example, the headpiece 600 includes two transmitter antennae, one in each of the two wrap-around ends 602, 603 and on receiver antenna, located in the housing 604. This configuration may be ideal for transmitting and receiving separately through the right and left hemispheres of the brain and detecting asymmetry between the hemispheres. In some uses, therefore, the VIPS system, such as the headpiece 600, may be used simply to detect that an asymmetry exists. This determination may be made at one point in time, as a "snapshot," or may be made over a period of time. The headset 600 or some other portion of the VIPS system may provide an alert or other message or data of some kind to a user, indicating that it has detected an asymmetry. This data may be used to help determine what next steps to take—for example, performing a CT scan on the patient, continuing to monitor the patient using the VIPS system and/or the like.

Other Applications

Although many embodiments of this disclosure describe VIPS technology for use in the measurement, monitoring, and/or detecting of fluid volume change, these same embodiments and/or alternative embodiments may use VIPS technology for the detection of non-fluid volume or change, such as a volume and/or change in a tissue in the patient's head. Furthermore, the association of fluid and/or volume change may or may not be a direct correlation to a pathology. Additional embodiments, for example, may not take into consideration any specific fluid, fluid volume, tissue or organ (example brain), but instead may assess the phase(s) and/or amplitude(s) change, and/or a combination of change(s). Such changes, volumes and the like may be defined and referred to as a "VIPS signature", which may correlate or be abstracted to a particular condition or pathology. For example, the effect of an ischemic stroke may not present as a volume/fluid change, but the VIPS technology may detect a frequency or frequencies and/or amplitude(s) signature indicative of an ischemic stroke. Furthermore, in some embodiments, the VIPS technology may detect a shift (or translation) of an organ of the body, for example a shift in the brain itself, which would present as a VIPS signature. There may be a number of different VIPS signatures, each relating to a different condition, abnormality, anatomy, physiology or the like. VIPS signatures may be defined as changes, thresholds, specific measurements and/or other parameters related to measured phase(s) and/or amplitude(s). In various embodiments, a VIPS device may include any number of predefined, stored VIPS signatures, and the device may compare phase and/or amplitude measurements to the VIPS signatures to determine whether a particular condition, abnormality, anatomy or physiology is present.

Other changes might be changes in properties of tissues/liquids, such as electrolytes, enzymes, glial fibers, phagocyte cells, and/or iron. For example, iron and protein content in tissue sometimes change after an injury (stroke, impact, bruise, etc.). In another example, cell membrane permeability may change, thus altering or breaking the sodium-potassium pump. Bio-electric potentials may change, osmotic pressure may change, etc. There are different phases to a stroke, for example, and with each there is continual "remodeling" of the injury site, which may or may not be solely dependent on fluid volume changes.

Although specific embodiments of the disclosure have been described herein for purposes of illustration, various modifications may be made without deviating from the spirit and scope of the disclosure. For example, although the present application includes several examples of monitoring fluid changes in the human brain as one potential application for the systems and methods described herein, the present disclosure finds broad application in a host of other applications, including monitoring fluid changes in other areas of the human body (e.g., arms, legs, lungs, etc.), in monitoring fluid changes in other animals (e.g., sheep, pigs, cows, etc.), and in other medical diagnostic settings. Fluid changes in an arm, for example, may be detected by having an arm wrapped in a bandage that includes a transmitter and a receiver.

A few examples of the other medical diagnostic settings in which the systems and methods described herein may be used include determining an absolute proportion of a particular fluid, tissue (e.g., muscle, fat, parenchymal organs, etc.), or other solid matter (e.g., a tumor) in a given area of a human body, determining relative permittivity and/or relative permeability of an object, and so forth. Further clinical applications include a wide variety of monitoring and diagnostic uses, including internal bleeding detection, distinction between different types of fluid (e.g. blood, extracellular fluid, intracellular fluid, etc.), assessing edema including cerebral edema as well as lymphedema, and assessing lung fluid build-up resulting from such conditions as congestive heart failure. All of these applications and many more may be addressed by various embodiments described herein. Accordingly, the scope of the claims is not limited to the specific examples given herein.

We claim:

1. A method for detecting a difference in bioimpedance between a left hemisphere and a right hemisphere of a brain of a patient, the method comprising:
    securing a headset of a volumetric integral phase-shift spectroscopy (VIPS) device to the patient's head to position a first transmitter on a left side of a posterior half of the patient's head, a second transmitter on a right side of a posterior half of the patient's head, and a receiver on the patient's forehead;
    transmitting a first VIPS spectrum of signals from the first transmitter through the left hemisphere of the patient's brain to the receiver;
    receiving the first transmitted VIPS spectrum of signals with the receiver;
    transmitting a second VIPS spectrum of signals from the second transmitter through the right hemisphere of the patient's brain to the receiver;
    receiving the second transmitted VIPS spectrum of signals with the receiver;
    sending a first received signal corresponding to the first transmitted VIPS spectrum of signals and a second received signal corresponding to the second transmitted VIPS spectrum of signals from the receiver to a processor coupled with the VIPS device;
    detecting, with the processor, a difference between the first received signal and the second received signal that corresponds to a difference between the left hemisphere and the right hemisphere of the patient's brain; and
    detecting the difference in bioimpedance between the left hemisphere and the right hemisphere with the processor, based on the difference between the left hemisphere and the right hemisphere.

2. The method of claim 1, further comprising determining, with the processor, that a stroke occurred in the left hemisphere or the right hemisphere of the brain, based on the detected difference in bioimpedance.

3. The method of claim 1, wherein detecting the difference between the left hemisphere and the right hemisphere comprises comparing a first fluid volume in the left hemisphere of the brain represented by the first received signal with a second fluid volume in the right hemisphere of the brain represented by the second received signal.

4. The method of claim 1, further comprising correlating the detected difference between the first received signal and the second received signal to a volumetric unit of measure by using a CT image as a transfer standard.

5. The method of claim 1, further comprising repeating the method multiple times over a period of time to monitor fluid volumes in the left hemisphere and the right hemisphere over the period of time to detect changes in the fluid volumes.

6. The method of claim 1, further comprising repeating the steps after a procedure is performed to treat a stroke in the left hemisphere or the right hemisphere of the patient's brain.

7. The method of claim 1, further comprising measuring a volume in at least one of the left hemisphere or the right hemisphere of the patient's brain that is within a range indicative of an abnormality.

8. The method of claim 7, wherein the volume is selected from the group consisting of a fluid volume, a solid volume, a tissue volume and a bulk volume.

* * * * *